United States Patent [19]

Weier et al.

[11] Patent Number: 5,427,932
[45] Date of Patent: Jun. 27, 1995

[54] REPEAT SEQUENCE CHROMOSOME SPECIFIC NUCLEIC ACID PROBES AND METHODS OF PREPARING AND USING

[75] Inventors: Heinz-Ulrich G. Weier, Tracy; Joe W. Gray, San Francisco, both of Calif.

[73] Assignee: Reagents of the University of California, Oakland, Calif.

[21] Appl. No.: 858,124

[22] Filed: Mar. 26, 1992

Related U.S. Application Data

[63] Continuation-in-part of Ser. No. 683,441, Apr. 9, 1991, abandoned.

[51] Int. Cl.$^6$ .................. C12P 19/34; C07H 21/04
[52] U.S. Cl. ......................... 435/91.2; 435/6; 435/810; 436/501; 536/22.1; 536/23.1; 536/24.3; 536/24.31; 536/24.33; 935/78; 935/88
[58] Field of Search ............... 435/6, 91, 291, 91.2, 435/810; 536/27–29, 22.1, 23.1, 24.21, 24.3, 24.31; 935/19, 78, 88; 436/501, 811

[56] References Cited

U.S. PATENT DOCUMENTS 4,683,195  7/1987  Mullis et al. ..................... 435/6

FOREIGN PATENT DOCUMENTS 9002821  3/1990  WIPO ............ C12Q 1/70
9008821  8/1990  WIPO ............ C12N 15/09

OTHER PUBLICATIONS

Wesley et al. (1990) Nucleic Acids Res., vol. 18, No. 3, pp. 599–603.
McDonald et al. (1990) Cell, vol. 61, pp. 991–1000.
Nat. Inst. of Health, (Derwent Abstract patent application Ser. No. 7,454,171), published May 15, 1990.
Baldini et al., "A Human Alpha Satellite DNA Subset Specific for Chromosome 12", *Am. J. Hum. Genet.*, 46: 784–788 (1990).
Buroker et al., "A Hypervariable Repeated Sequence on Human Chromosome 1p. 36", *Hum. Genet*, 77: 175–181 (1987).
Cooke and Hindley, "Cloning of Human Satellite III DNA: Different Components are on Different Chromosomes", *Nucleic Acids Research*, 6 (10): 3177–3197 (1979).
Cremer et al., "Detection of Chromosome Aberrations in the Human Interphase Nucleus by Visualization of Specific Target DNAs with Radioactive and Non-radioactive In Situ Hybridization Techniques: Diagnosis of Trisomy 18 with Probe L1.84", *Hum. Gene*, 74: 346–352.

(List continued on next page.)

*Primary Examiner*—Margaret Parr
*Assistant Examiner*—Ardin H. Marschel
*Attorney, Agent, or Firm*—Leona L. Lauder; Richard E. Cuellar; Nora A. Hackett

[57] ABSTRACT

A primer directed DNA amplification method to isolate efficiently chromosome-specific repeated DNA wherein degenerate oligonucleotide primers are used is disclosed. The probes produced are a heterogeneous mixture that can be used with blocking DNA as a chromosome-specific staining reagent, and/or the elements of the mixture can be screened for high specificity, size and/or high degree of repetition among other parameters. The degenerate primers are sets of primers that vary in sequence but are substantially complementary to highly repeated nucleic acid sequences, preferably clustered within the template DNA, for example, pericentromeric alpha satellite repeat sequences. The template DNA is preferably chromosome-specific. Exemplary primers ard probes are disclosed. The probes of this invention can be used to determine the number of chromosomes of a specific type in metaphase spreads, in germ line and/or somatic cell interphase nuclei, micronuclei and/or in tissue sections. Also provided is a method to select arbitrarily repeat sequence probes that can be screened for chromosome-specificity.

13 Claims, 7 Drawing Sheets

OTHER PUBLICATIONS

Dahl et al., "Application of DNA-DNA Hybridization of Dual Labeled Probes to the Detectioni of Trisomy 21, Monosomy 21, and Sex Determination", *Am. J. Hum. Genet.*, 43: 502–510 (1988).

Devilee et al., "Sequence Heterogeneity Within the Human Alphoid Repetitive DNA Family", *Nucleic Acids Research*, 14 (5): 2059–2073 (1986).

Devileee et al., "Chromosome-Specificic Alpha Satellite DNA: Isolation and Mapping of A Polymorphic Alphoid Repeat from Human Chromosome 10", *Genomics*, 3: 1–7 (1988).

Frommer et al., "Localisation of Satellite DNA Sequences on Human Metaphase Chromosomes Using Bromodeoxyuridine-Labelled Probes", *Chromosoma* (Berl), 97: 11–18 (1988).

Goonewardena et al., "Use of PCR with Y-Specific Probes for Rapid Sex Determination", *Am. J. Hum. Genet.*, 45 (4) (Suppl): A-190 (Oct. 1989).

Guatelli et al., "Isothermal In Vitro Amplification of Nucleic Acids by a Multienzyme Reaction Modeled After Retroviral Replication", *PNAS* (USA), 87: 1874–1878 (Mar. 1990).

Green and Olsen, "Systematic Screening of Yeast Artificial-Chromosome Libraries by Use of the Polymerase Chain Reaction", *PNAS* (USA), 87: 12–1217 (Feb. 1990).

Harper et al., "Detection of Numerical Chromosome Aberrations in Bladder Cancer by In Situ Hybridization", *PNAS* (USA), 78 (7): 4458–4460 (Jul. 1981).

Hopman, et al., "Detection of Numerical Chromosome Aberrations in Bladder Cancer by In Situ Hibridization", *American Journal of Pathology*, 135 (6): 1105–1117 (Dec. 1989).

Hulsebos et al., "Isolation and Characterization of Alphoid DNA Sequences Specific for the Pericentric Regions of Chromosomes 4, 5, 9, and 19", *Cytogenet. Cell Genet.*, 47: 144–148 (1988).

Jorgensen et al., "Chromosome-Specific Subfamilies Within Human Alphoid Repetitive DNA", *J. Mol. Biol.*, 187: 185–196 (1986).

Koch et al., "Oligonucleotide-Priming Methods for the Chromosome-Specific Labelling of Alpha Satellite DNA In Situ", *Chromosoma* (Berl), 98: 259–265 (1989).

Lichter et al., "Fluorescence In Situ Hybridization with Alu and L1 Polymerase Chain Reaction Probes for Rapid Characterization of Human Chromosomes in Hybrid Cell Lines", *PNAS* (USA), 87: 6634–6638 (Sep. 1990).

Liang and Johnson, "Rapid Plasmid Insert Amplification with Polymerase Chain Reaction", *Nucleic Acids Research*, 16 (8): 3579 (1988).

Manuelidis, "Chromosomal Localization of Complex and Simple Repeated Human DNAs", *Chromosoma* (Berl), 66: 23–32 (1978).

Meyne and Moyzis, "Human Chromosome-Specific Repetitive DNA Probes: Targeting In Situ Hybridization to Chromosome 17 with a 42-Base-Pair Alphoid DNA Oligomer", *Genomics*, 4: 472–478 (1989).

Moyzis et al., "The Distribution of Interspersed Repetitive DNA Sequences in the Human Genome", *Genomics*, 4: 273–289 (1989).

Murray and Martin, "Nucleotide Sequences of Human α-DNA Repeats", *Gene*, 57: 255–259 (1987).

Nakahori et al., "A Human Y-Chromosome Specific Repeated DNA Family (DYZI) Consists of a Tandem Array of Pentanucleotides", *Nucleic Acids Research*, 14 (19): 7569–7580 (1986).

Reis et al., "Human Alphoid Family of Tandemly Repeated DNA Sequence of Cloned Tetrameric Fragments and Analysis of Familiar Divergence", *J. Mol. Biol.*, 186: 31–41 (1985).

Saiki et al., "Primer-Directed Enzymatic Amplification of DNA with a Thermostable DNA Polymerase", *Science*, 239: 487–491 (Jan. 29, 1988).

Smith et al., "Repeated DNA of the Human Y Chromosome", *Development*, 101 (Suppl): 77–92 (1987).

van Dekken et al., "Targeted Cytogenetic Analysis of Gastric Tumors by In Situ Hybridization With a Set of Chromosome-Specific DNA Probes", *Cancer*, 66: 491–497 (Aug. 1, 1990).

Walker et al., "Isothermal In Vitro Amplification of DNA by a Restriction Enzyme/DNA Polymerase System", *PNAS* (USA), 89: 392–396 (Jan. 1992).

(List continued on next page.)

OTHER PUBLICATIONS

Warburton et al., "PCR Amplification of Chromososome-Specific Alpha Satellite DNA: Definition of Centromeric STS Markers and Polymorphic Analysis", *Genomics, 11*: 324–333 (1991).

Waye and Willard, "Chromosome-Specific Alpha Satellite DNA: Nucleotide Sequence Analysis of the 2.0 Kilobasepair Repeat from the Human X Chromosome", *Nucleic Acids Research, 13* (8): 2731–2743 (1985).

Waye and Willard, "Structure, Organization, and Sequence of Alpha Satellite DNA from Human Chromosome 17: Evidence for Evolution by Unequal Crossing-Over and an Acenstral Pentamer Repeat Shared with the Human X Chromosome", *Molecular and Cellular Biology, 6* (9): 3156–3165 (Sep. 1986).

Waye and Willard, "Nucleotide Sequence Heterogeneity of Alpha Satellite Repetitive DNA: A Survey of Alphoid Sequences from Different Human Chromosomes", *Nucleic Acids Research, 15* (18): 7549–7569 (1987).

Waye and Willard, "Chromosome Specificity of Satellite DNAs: Short-and Long-Range Organization of a Diverged Dimeric Subset of Human Alpha Satellite from Chromosome 3", *Chromosoma* (Berl), 97: 475–480 (1989).

Waye et al., "Chromosome-Specific Alpha Satellite DNA from Human Chromosome 1: Hierarchical Structure and Genomic Organization of a Polymorphic Domain Spanning Several Hundred Kilobase Pairs of Centromeric DNA", *Genomics, 1*: 43–51 (1987).

Waye et al., "Organization and Evolution of Alpha Satellite DNA from Human Chromosome 11", Chromosoma, 95: 182–188 (1987).

Weier and Gray, "A Programmable System to Perform the Polymerase Chain Reaction", DNA, 7 (6): 441–447 (1988).

Weier and Gray, "Generation of Chromosome-Specific DNA Probes by In Vitro DNA Amplification Using Sorted Chromosomes", *The Journal of the Society for Analytical Cytology: Cytometry* (Suppl. 4): 57 (Abstract No. 361B) (1990).

Weier and Rosette, "Generation of Labeled RNA Probes from Enzymatically Amplified DNA Templates", *Nucleic Acids Research, 16* (24): 11836 (1988).

Weier and Rosette, "Generation of Clonal DNA Templates for In Vitro Transcription Without Plasmid Purification", *BioTechniques, 8* (3): 252–257 (1990).

Weier et al., "Synthesis of Y Chromosome-Specific Labeled DNA Probes by In Vitro DNA Amplification", *Journal of Histochemistry and Cytochemistry, 38* (3): 421–426 (1990).

Willard, "Chromosome-Specific Organization of Human Alpha Satellite DNA", *Am. J. Hum. Genet., 37*: 524–532 (1985).

Willard and Waye, "Hierarchical Order in Chromosome-Specific Human Alpha Satellite DNA", *TIG, 3* (7): 192–198 (Jul. 1987).

Willard et al., "Isolation and Characterization of a Major Tandem Repeat Family from the Human X Chromosome", *Nucleic Acids Research, 11* (7): 2017–2033 (1983).

Yang et al., "Characterization of a Cloned Repetitive DNA Sequence Concentrated on the Human X Chromosome", *PNAS* (USA), 79: 6593–6597 (Nov. 1982).

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: NUCLEIC ACID PRIMER ( i i i ) HYPOTHETICAL: NO ( i v ) ANTI-SENSE: NO ( x ) PUBLICATION INFORMATION:
( A ) AUTHORS: Weier et al.

(B) TITLE: "Two-color hybridization with high complexity chromosome- specific probes and a degenerate alpha satellite probe DNA allows unambiguous discrimination between symmetrical and asymmetrical translocations"
(C) JOURNAL: Chromosoma
(D) VOLUME: 100
(F) PAGES: 371-376
(G) DATE: 1991

(xi) SEQUENCE DESCRIPTION: SEQ ID NO:1:

GAAGCTTA W S TMACAGAGTT KAA    23

(2) INFORMATION FOR SEQ ID NO:2:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: NUCLEIC ACID PRIMER (iii) HYPOTHETICAL: NO (iv) ANTI-SENSE: NO (x) PUBLICATION INFORMATION:
(A) AUTHORS: Weier et al.
(B) TITLE: "Two-color hybridization with high complexity chromosome- specific probes and a degenerate alpha satellite probe DNA allows unambiguous discrimination between symmetrical and asymmetrical translocations"
(C) JOURNAL: Chromosoma
(D) VOLUME: 100
(F) PAGES: 371-376
(G) DATE: 1991

(xi) SEQUENCE DESCRIPTION: SEQ ID NO:2:

GCTGCAGATC MCMAAGHAGT TTC    23

(2) INFORMATION FOR SEQ ID NO:3:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: NUCLEIC ACID PRIMER (iii) HYPOTHETICAL: NO (iv) ANTI-SENSE: NO (xi) SEQUENCE DESCRIPTION: SEQ ID NO:3:

CCCGGATCCC TGCAGAAGCT TA W STMACA    29

(2) INFORMATION FOR SEQ ID NO:4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: NUCLEIC ACID PRIMER (iii) HYPOTHETICAL: NO (iv) ANTI-SENSE: NO (xi) SEQUENCE DESCRIPTION: SEQ ID NO:4:

CCCGGATCCA AGCTTCTGAG ATCMCMAA    28

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: NUCLEIC ACID PRIMER ( i i i ) HYPOTHETICAL: NO ( i v ) ANTI-SENSE: NO ( x ) PUBLICATION INFORMATION:
        ( A ) AUTHORS: Weier et al.
        ( B ) TITLE: "Non-Isotopical Labeling of Murine
            Heterochromation In Situ by Hybridization with In
            Vitro Synthesized Biotinylated Gamma (Major)
            Satellite DNA"
        ( C ) JOURNAL: BioTechniques
        ( D ) VOLUME: 10
        ( E ) ISSUE: 4
        ( F ) PAGES: 498-505
        ( G ) DATE: 9-APR-91

( x i ) SEQUENCE DESCRIPTION: SEQ ID NO:5:

CCCAAGCTTG AAATGTCCAC T                                        2 1

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: NUCLEIC ACID PRIMER ( i i i ) HYPOTHETICAL: NO ( i v ) ANTI-SENSE: NO ( x ) PUBLICATION INFORMATION:
        ( A ) AUTHORS: Weier et al.
        ( B ) TITLE: "Non-Isotopical Labeling of Murine
            Heterochromation In Situ by Hybridization with In
            Vitro Synthesized Biotinylated Gamma (Major)
            Satellite DNA"
        ( C ) JOURNAL: BioTechniques
        ( D ) VOLUME: 10
        ( E ) ISSUE: 4
        ( F ) PAGES: 498-505
        ( G ) DATE: 9-APR-91

( x i ) SEQUENCE DESCRIPTION: SEQ ID NO:6:

CCCAAGCTTT TTCTTGCCAT A                                        2 1

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: NUCLEIC ACID PRIMER ( i i i ) HYPOTHETICAL: NO ( i v ) ANTI-SENSE: NO ( x i ) SEQUENCE DESCRIPTION: SEQ ID NO:7:

CTCGGAATTA ACCCTCACTA AAGG                                      2 4

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: NUCLEIC ACID PRIMER (iii) HYPOTHETICAL: NO (iv) ANTI-SENSE: NO (x) PUBLICATION INFORMATION:
        (A) AUTHORS: Weier et al.
        (B) TITLE: "Non-Isotopical Labeling of Murine
            Heterochromation In Situ by Hybridization with In
            Vitro Synthesized Biotinylated Gamma (Major)
            Satellite DNA"
        (C) JOURNAL: BioTechniques
        (D) VOLUME: 10
        (E) ISSUE: 4
        (F) PAGES: 498-505
        (G) DATE: 9-APR-91

(xi) SEQUENCE DESCRIPTION: SEQ ID NO:8:

GAATTGTAAT ACGACTCACT ATAG          24

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: NUCLEIC ACID PRIMER (iii) HYPOTHETICAL: NO (iv) ANTI-SENSE: NO (xi) SEQUENCE DESCRIPTION: SEQ ID NO:9:

TCGAAACGGG TATATGCTCA CGTAAAA        27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: NUCLEIC ACID PRIMER (iii) HYPOTHETICAL: NO (iv) ANTI-SENSE: NO (xi) SEQUENCE DESCRIPTION: SEQ ID NO:10:

AAGACAGTTT CAAAACTGCT CCATCAA        27

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: NUCLEIC ACID PRIMER (iii) HYPOTHETICAL: NO (i v) ANTI-SENSE: NO (x i) SEQUENCE DESCRIPTION: SEQ ID NO:11:

GGATAGCTTA ACGATTTCGT TGGAAAC                                      27

(2) INFORMATION FOR SEQ ID NO:12:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: NUCLEIC ACID PRIMER (i i i) HYPOTHETICAL: NO (i v) ANTI-SENSE: NO (x i) SEQUENCE DESCRIPTION: SEQ ID NO:12:

CAAACGTGCT CAAAGTAAGG GAATG                                        25

(2) INFORMATION FOR SEQ ID NO:13:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (i i) MOLECULE TYPE: NUCLEIC ACID PRIMER (i i i) HYPOTHETICAL: NO (i v) ANTI-SENSE: NO (x i) SEQUENCE DESCRIPTION: SEQ ID NO:13:

ATGGAATTGA ATGGAACGGA ATAGAGT                                      27

(2) INFORMATION FOR SEQ ID NO:14:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (i i) MOLECULE TYPE: NUCLEIC ACID PRIMER (i i i) HYPOTHETICAL: NO (i v) ANTI-SENSE: NO (x i) SEQUENCE DESCRIPTION: SEQ ID NO:14:

CGATTCCATT CAATTCGAGA CCATTCT                                      27

(2) INFORMATION FOR SEQ ID NO:15:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (i i) MOLECULE TYPE: NUCLEIC ACID PRIMER (i i i) HYPOTHETICAL: NO (i v) ANTI-SENSE: NO (x i) SEQUENCE DESCRIPTION: SEQ ID NO:15:

CCCAAGCTTG CATGCGAATT CNNNNCAGG                                    29

( 2 ) INFORMATION FOR SEQ ID NO:16:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( i i ) MOLECULE TYPE: GENOMIC DNA —human alpha satellite
               monomer consensus sequence ( i i i ) HYPOTHETICAL: NO ( i v ) ANTI-SENSE: NO ( x ) PUBLICATION INFORMATION:
        ( A ) AUTHORS: Willard and Waye
        ( B ) TITLE: "Hierarchial order in chromosome-specific
               human alpha satellite DNA"
        ( C ) JOURNAL: Trends in Genet.
        ( D ) VOLUME: 3
        ( E ) ISSUE:
        ( F ) PAGES: 192-198
        ( G ) DATE: 1987

( x i ) SEQUENCE DESCRIPTION: SEQ ID NO:16:

```
AACTCACAGA GTTGAACMTT YCTTTTSATA GAGCAGTTTK GAAACACTCT TTTTGTAGAA      60

TCTGCAAGTG GAYATTTGGA SCKCTTTGAG GMYT W YGKTG GAAAMGGRAA TATCTTCAYA   120

TAAAANCTAR ACAGAAGCAT TCTCAGAAAC TTCTTTGTGA T                         161
```

( 2 ) INFORMATION FOR SEQ ID NO:17:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( i i ) MOLECULE TYPE: GENOMIC DNA ( i i i ) HYPOTHETICAL: NO ( i v ) ANTI-SENSE: NO ( x i ) SEQUENCE DESCRIPTION: SEQ ID NO:17:

```
GGATCCCTGC AGAAGCTTAA GTCACAGAGT TGAACCTTCC TTTAGACAGA GCAGTTTGA       60

AAAATTCTTT CTGTGGAATC TGCAAGTGGA GATTTCAAGC GATTTGAGGC TAATCTTTGA    120

AATGGAAATA TCCTCGTGTA AAAACTACAC AGAATCATTC TCAGAAACTA CTTGGGGATC    180

TGCAGAAGCT TGGATCC                                                   197
```

( 2 ) INFORMATION FOR SEQ ID NO:18:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( i i ) MOLECULE TYPE: GENOMIC DNA ( i i i ) HYPOTHETICAL: NO ( i v ) ANTI-SENSE: NO ( x i ) SEQUENCE DESCRIPTION: SEQ ID NO:18:

```
GGATCCCTGC AGAAGCTTAT GTAACAGAGT TGAACCTTCC TTTAGACAGA GCAGTTTGA       60

AAAACTCTTT CTGTGGAATT TGCAAGTGGA GATTTCAAGC GATTTGAGGC TAATCTTTGA    120

AATGGAAATA TCTTCGTGTA AAAACTACAC AGAATCATTC TCAGAAACTT CTTGGTGATC    180
```

TGCAGAAGCT TGGATCC                                                              197

( 2 ) INFORMATION FOR SEQ ID NO:19:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: GENOMIC DNA -- chromosome 12-specific
        alphoid monomer sequence ( i i i ) HYPOTHETICAL: NO ( i v ) ANTI-SENSE: NO ( x ) PUBLICATION INFORMATION:
        ( A ) AUTHORS: Baldini et al.
        ( B ) TITLE: "High-resolution Alu banding of human
            chromosomes with biotinylated Alu-PCR products:
            use for in situ hybridization mapping"(Abstract)
        ( C ) JOURNAL: Am. J. Hum. Genet
        ( D ) VOLUME: 46 (Suppl.)
        ( F ) PAGES: A87
        ( G ) DATE: 1990

( x i ) SEQUENCE DESCRIPTION: SEQ ID NO:19:

CAACTCAAGG TGTTTAAGCT TTCTTTTCAT AGAGTAGTTT GGAAACACTC TGTCTGTAAA        60

GTCTGCAAGC AGATATTTGG ACCTCTTTGG GGCCTTCGTT GGAAACGGGN ATTTCTTCAT        120

AGAANCGCTA GAAAGAAGAA TACTGAGTAA GTTCTTTGTG TTGCCTCTAT T                171

( 2 ) INFORMATION FOR SEQ ID NO:20:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: GENOMIC DNA -- chromosome 12-specific
        alphoid monomer sequence ( i i i ) HYPOTHETICAL: NO ( i v ) ANTI-SENSE: NO ( x ) PUBLICATION INFORMATION:
        ( A ) AUTHORS: Baldini et al.
        ( B ) TITLE: "High-resolution Alu banding of human
            chromosomes with biotinylated Alu-PCR products:
            use for in situ hybridization mapping"(Abstract)
        ( C ) JOURNAL: Am. J. Hum. Genet
        ( D ) VOLUME: 46 (Suppl.)
        ( F ) PAGES: A87
        ( G ) DATE: 1990

( x i ) SEQUENCE DESCRIPTION: SEQ ID NO:20:

CAACTCACAG AGGTGAACTG TCCTTTAGAC AGAGCAGATG TGAAACCCTC TTTTTGTGAT        60

ATTTGCAGGT GGAGATTTCA AGCGCTTTTA GGCCAAATGT AGAAAAGGAA ATATCTTCGT        120

ATAAAAACTA GACAGAATCA TTCTCAGAAA CTACTTTGTG ATGTGTGCGT T                171

( 2 ) INFORMATION FOR SEQ ID NO:21:

( i ) SEQUENCE CHARACTERISTICS:
        ( A ) LENGTH: 174 base pairs
        ( B ) TYPE: nucleic acid
        ( C ) STRANDEDNESS: single
        ( D ) TOPOLOGY: linear ( i i ) MOLECULE TYPE: GENOMIC DNA -- chromosome 12-specific
        alphoid monomer sequence (iii) HYPOTHETICAL: NO (iv) ANTI-SENSE: NO (x) PUBLICATION INFORMATION:
(A) AUTHORS: Baldini et al.
(B) TITLE: "High-resolution Alu banding of human
chromosomes with biotinylated Alu-PCR products:
use for in situ hybridization mapping"(Abstract)
(C) JOURNAL: Am. J. Hum. Genet
(D) VOLUME: 46 (Suppl.)
(F) PAGES: A87
(G) DATE: 1990

(xi) SEQUENCE DESCRIPTION: SEQ ID NO:21:

```
CAATTCACAG AGATAACCTT TCTTTTNGAT GAAGGAGTTT GGAGACACTG TGTTTGTAAA       60

GTCTGCAAGT GGATATTTGG ACCTCTTTGA GGCCTTCGTT GGAAGGAAAC GGGATTTCTT      120

CCTGTAANTG TTCGACAGAA GAATTCTCAG TAACTTATTT GTGGTGTGTG TATT           174
```

(2) INFORMATION FOR SEQ ID NO:22:

(i) SEQUENCE CHARACTERISTICS:
(A) LENGTH: 171 base pairs
(B) TYPE: nucleic acid
(C) STRANDEDNESS: single
(D) TOPOLOGY: linear (ii) MOLECULE TYPE: GENOMIC DNA -- chromosome 12-specific
alphoid monomer sequence (iii) HYPOTHETICAL: NO (iv) ANTI-SENSE: NO (x) PUBLICATION INFORMATION:
(A) AUTHORS: Baldini et al.
(B) TITLE: "High-resolution Alu banding of human
chromosomes with biotinylated Alu-PCR products:
use for in situ hybridization mapping"(Abstract)
(C) JOURNAL: Am. J. Hum. Genet
(D) VOLUME: 46 (Suppl.)
(F) PAGES: A87
(G) DATE: 1990

(xi) SEQUENCE DESCRIPTION: SEQ ID NO:22:

```
CAACTCACAG AGTTGAACCT TCCTTTAGAC AGAGCAGATT TGAAACACCC TATTTGTGCA       60

GTTTCCAGTT GGAGATTTCA ATCACTTTGA GACCAAATGT ACAAAAGGAA ACATCTTCGT      120

ATAAAAACTA GACAGAATCA TTCTCAGAAA CTACTTTGTG ATGTGTGCGT T              171
```

REPEAT SEQUENCE CHROMOSOME SPECIFIC NUCLEIC ACID PROBES AND METHODS OF PREPARING AND USING

The United States Government has rights in this invention pursuant to Contract No. W-7405-ENG-48 between the United States Department of Energy and the University of California for the operation of Lawrence Livermore National Laboratory.

RELATED APPLICATIONS

This application is a continuation-in-part application of U.S. Ser. No. 07/683,441 filed Apr. 9, 1991, now abandoned. Priority in said prior filed applications is herein claimed.

BACKGROUND OF THE INVENTION

The cytogenetic analysis of human cells and tissue material is typically based on microscopic inspection of banded metaphase chromosomes [Buckton and Evans 1973]. Cell samples taken from human tumors, however, usually contain too few cells in metaphase, so that mitogens have to be used to stimulate cellular proliferation. In solid tumors, stimulation of cellular growth of interphase cells is especially difficult or cannot be achieved at all [Gahrton et al. 1980; Trent 1985; Knuutila et al. 1986]. Cytogenetic analyses by means of in situ hybridization with chromosome-specific nucleic acid probes facilitate the differentiation between tumor cells and normal cells by allowing the analysis of interphase nuclei. Such analyses reduce the time and labor required for preparation of metaphase chromosomes and minimizes selection that may occur during cell culture [Cremer et al. 1986; Pinkel et al. 1986; Hopman et al. 1988; Trask et al. 1988; Nederlof et al. 1989].

Cloned probes suitable for chromosome-specific hybridization have now been reported for more than two-thirds of the human chromosomes. Some of such probes are specific for human satellite III DNA sequences [Cooke and Hindley 1979; Berdize 1987; Weier et al. 1990]. However, most of such probes bind to alpha satellite DNA found at or near the chromosome centromeres (pericentromeric) [Manuelidis 1978; Willard and Waye 1987]. The alphoid DNA sequences are comprised of tandemly repeated monomers of about 171 base pairs (bp) [Wu and Manuelidis 1980]. Certain parts of the 171 bp alphoid monomers appear to be conserved among all human chromosomes. Others, possibly organized as higher order repeats, show substantial chromosome-specific variation and may be used as the target of chromosome-specific probes [Devilee et al. 1986; Jorgensen et al., 1986; Murray and Martin 1987; Willard and Waye 1987]. Some authors have suggested that the chromosome-specificity is associated with organization of individual monomers in higher order repeats [Waye et al., 1987a and 1987b; Willard and Waye 1987; Hulsebos et al. 1988]. However, there is evidence that some monomers are sufficiently specific and so highly repeated that they can be used as a hybridization target for interphase chromosome enumeration [Meyne and Moyzis 1989].

Many of the probes reported so far allow ready analysis of chromosome copy number [Choo et al. 1990. Others, however, show considerable cross-hybridization with non-target chromosomes and may require hybridization at elevated levels of stringency [Waye et al. 1987b; Devilee et al. 1988]. Under such conditions, signal intensities often decrease, so that such probes cannot be used in critical applications, for example, when hybridizing to highly condensed sperm chromatin [Wyrobek et al. 1990] or tissue sections wherein probe diffusion is poor [Emmerich et al. 1989] or when the hybridization target cannot be tightly controlled due partially to degradation of the cellular material.

Important probe parameters besides high specificity for the target chromosome type are the size of the probe molecule and the extent of the hybridization target area measured in base pairs (bp). For example, individual probe molecules may need to be of a size that favors diffusion into densely packed chromatin of sperm. Relatively short probe molecules that are complementary to highly reiterated DNA target sequences, such as the repeated satellite DNA, enable high signal intensities through binding of a large number of probe molecules to the target DNA without jeopardizing specificity. The preferred probes render highest possible signal-to-noise ratio.

The instant invention provides a primer directed DNA amplification method using the polymerase chain reaction (PCR) [Saiki et al. 1988b] with degenerate primers as an efficient means to isolate chromosome-specific repeated DNA. In the absence of any a priori knowledge other than the type of DNA repeat, for example, alpha satellite DNA, the methods of this invention allow the generation of chromosome-specific repeat sequence probe DNA. Disclosed are representative probes for human chromosome-specific alphoid DNA that have high specificity with high signal intensities in in situ hybridization experiments. In representative methods of this invention degenerate PCR primers for two conserved regions of the 171-bp alphoid monomer are used to amplify alphoid DNA from flow-sorted chromosome-specific DNA. The probes can be labeled by amplifying in the presence of modified dNTPs, or they can be labeled after completion of the PCR reaction by chemical or enzymatic modification of the PCR products.

Weier et al. (1990) described the use of in vitro DNA amplification for production of double-stranded, biotin-labeled DNA probes. In that article a 124 bp segment of the Y chromosome-specific 3.4 kb repeat was amplified from human genomic DNA using PCR with nondegenerate primers.

Koch et al. (1989) disclosed a DNA analysis method called Primed Amplification Labeling (PAL) in which biotin-labeled hybridization probes are produced in a polymerase chain reaction (PCR), in which two synthetic oligonucleotide primers anneal within the same alphoid monomer. If DNA from a specific chromosome is used as the template, Koch et al. reported that the resulting probe mixture "gives stronger and more chromosome-specific signals in in situ hybridization experiments than does a cloned alpha satellite DNA probe derived from the same chromosome." [Abstract, p. 259.]

The instant method differs from the Koch et al. PAL method in several substantial ways. The primers used by Koch et al. are different from those of the instant invention, not only in the location of the primer annealing sites within the consensus monomer and the direction of primer extension, but, more importantly, the Koch et al. primers are nondegenerate. Thus, the amplification scheme described by Koch et al. is likely to amplify a rather limited number of different alphoid DNA sequences, and under typical PCR conditions, would not allow amplification of the cloned DNA fragments, for example, those in pBS609-51 and pBS609-52 discussed infra which have base pair mismatches.

Specifically disclosed herein are representative probes for chromosome 8-specific and chromosome 10-specific alphoid DNAs. An alphoid DNA fragment, pJM128, that is enriched on human chromosomes 8 has been isolated from a human DNA library and is described in the literature [Donlon et al. 1987]. That probe, however, shows considerable crosshybridization with other human chromosomes complicating its use in interphase analysis [Donlon et al. 1987].

Further disclosed herein are experiments with unpurified representative probes demonstrating their specificity in competitive hybridization protocols with unlabeled genomic alphoid DNA and/or total genomic DNA. The use of such probes for enumeration of chromosomes in normal and tumor cell nuclei is also shown.

Probe DNA molecules prepared according to the methods of this invention were cloned and analyzed by a combination of in vitro DNA amplification, dideoxynucleotide sequencing and in situ hybridization. Probes were screened for specificity, repeat content and size, among other parameters. Representative monomeric probe molecules prepared according to the methods of this invention may have more than 80% homology with the alphoid consensus sequence or published alphoid monomers that map to different human chromosomes, but they show unprecedented specificity for highly reiterated DNA sequences on human chromosomes. The methods of this invention produce probes and collections of probes to highly repeated sequences such that the signal is much brighter and stronger than from a cloned repeat sequence probe that was prepared by conventional techniques.

SUMMARY OF THE INVENTION

Described herein are primer directed DNA amplification methods using degenerate primers to isolate efficiently chromosome-specific repeated DNA. The methods of this invention provide for the generation of chromosome-specific repeat sequence nucleic acid probes. Representative probes of this invention are repeat sequence probes for human chromosome-specific alphoid DNA.

Methods are provided to prepare chromosome-specific repeat sequence nucleic acid probes comprising:
  binding a first set of degenerate oligonucleotide primers to repeat sequence units in template DNA that is chromosome-specific;
  binding a second set of degenerate oligonucleotide primers to said repeat sequence units such that each of the 5' ends of said first set of primers faces a 5' end of one of said second set of primers, and the binding sites of said first set of primers are within a distance of from about 20 bp to about 5 kilobases (kb) of the binding sites of said second set of primers; and
  amplifying the template DNA by a polymerase chain reaction (PCR) method between and including the first and second set of primers to produce chromosome-specific repeat sequence nucleic acid probes. Those probes can be prepared to be specific for any chromosomes that have said repeat sequences. Preferably, those probes are specific for human chromosomes 1 through 22, X and Y.

Preferably, the repeat sequence units are clustered and more preferably, said clustered repeat sequence units are alphoid monomers. Representative preferred degenerate primers are WA1 and WA2 and/or WA11 and WA12 as shown in Table I, among others. Preferably, the template DNA is chromosome-specific DNA; preferably, the chromosome-specific template DNA has been flow-sorted, isolated by microdissection, isolated by density gradients or is in a hybrid cell.

The probes can be labeled by performing the amplification step, at least in the later PCR cycles, in the presence of modified dNTPs, for example, they can be labeled with biotin or digoxigenin by amplifying in the presence of biotin-11-dUTP or digoxigenin-11-dUTP, respectively [Weier et al. 1990]. Alternatively, the probes can be labeled after completion of the PCR reaction by chemical or enzymatic modification of the PCR products [for example, as shown in Landegent et al. 1984; and Weier et al. 1991b].

Further disclosed are primers for preparing the probes of this invention, and the probes themselves. Still further disclosed are methods of using the probes of this invention. In these methods, unlabeled blocking DNA, for example, human genomic DNA, Cot 1 DNA and/or human alphoid DNA, is used to reduce crosshybridization.

The high specificity repeat sequence probes once separated from the genomic DNA, as a heterogeneous mixture of amplification products, can be screened for high specificity and other desirable probe parameters. They can be further amplified by a variety of methods including PCR and related methods. Cloned probes can be screened by, for example, gel electrophoresis for appropriate sizes. Selected clones are preferred templates for generating highly specific repeat sequence probes. To amplify said selected clones, it is preferred that the templates be inserted in a vector with appropriate flanking sequences that are homologous to primers for PCR amplification. For example, if the selected probe is cloned in a Bluescribe plasmid [pBS; Stratagene, La Jolla, Calif. (USA)], the primers WBS2 and WBS4 can be used to generate the selected probe.

The probes of this invention are useful in enumerating specific chromosomes in interphase nuclei (both of germ line cells and somatic cells), micronuclei, metaphase spreads and/or tissue sections. When the probes are prepared in a method using degenerate primers to the alphoid consensus monomer, they are termed degenerate alpha satellite probes or das probes. Such das probes depending upon the chromosome-specific template DNA from which they were prepared can be used to stain the pericentromeric and/or centromeric regions of specific chromosomes, for example, any of the human chromosomes 1 through 22, X and Y.

Further, a method to select repeat probes arbitrarily is herein disclosed wherein a specific primer Jun1 which binds to DNA sequences having the repeat unit CAGG, is used in a PCR reaction with genomic and/or chromosome-specific DNA as template.

Any of various conventional labeling techniques, direct or indirect, may be used on the described probes, including fluorescent chemicals, radioactive materials, chemical haptens, or enzymatic amplifiers. More than one label may be employed.

A. A biotinylated probe DNA was generated by PCR using isolated human chromosomes as amplification template. Metaphase spreads from lymphocytes from a normal donor showed hybridization of probe DNA with repeated DNA probe DNA in the centromeric region of chromosomes 10. There is, however, binding of probe molecules to repeated DNA at or near the centromeres of other chromosomes.

B. Interphase cell nuclei were hybridized with a mixture containing the biotinylated, chromosome 10 alpha satellite DNA probe shown in (A) in combination with a digoxigenin labeled probe for DNA of the Alu repeat family. The nuclei are shown with binding of the biotinylated alpha satellite DNA to numerous sites.

C. The probe specificity was increased by blocking the binding of less specific DNA fragments. Metaphase spreads from lymphocytes from a normal donor showed that the biotinylated probe DNA hybridizes preferentially with repeated DNA in the centromeric region of chromosomes 10 (arrows) when the hybridization mixture contained unlabeled total human alphoid DNA.

D. Hybridization of the AAF-labeled DNA to a single cell suspension of human kidney cells. The cell material was obtained by enzymatic digestion of tissue adjacent to an aneuploid tumor. Interphase cell nuclei with the normal complement of 2 copies of chromosomes 10 showed two bright spots delineating domains of chromosome 10-specific alphoid DNA, when the degenerate probe DNA was hybridized in the presence of human genomic DNA as blocking agent.

E. Some of the cells in the preparation shown in (D) showed three domains of bound probe indicating the presence of an extra copy of chromosome 10 in those cells.

F. Biotinylated degenerate probe DNA was hybridized to deparaffinized serial sections of ovarian cancer tissue.

G. The clonal probe DNA pBS609-51 was biotinylated and hybridized without blocking DNA to serial sections from an ovarian tumor.

H. Metaphase spreads revealed exclusive binding of DNA from another clone (pBS609-13) to the centromeric region of human chromosome 10.

I. The digoxigenin labeled probe prepared from the bacterial clone pBS609-51 bound very specifically to DNA in the centromeric region of chromosomes 10 without signs of crosshybridization to alphoid DNA domains on other chromosomes.

Figure 5:
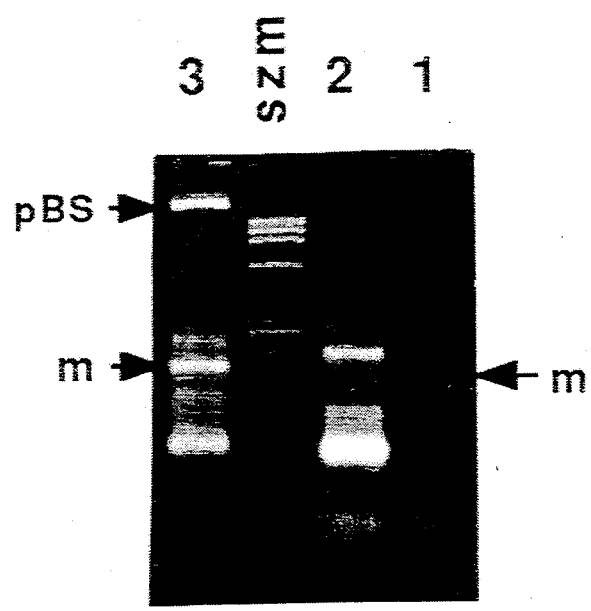

FIG. 5 shows the size distribution of in vitro DNA amplification products using primers WA1 and WA2, and isolated human chromosome 10 as the amplification template; (lane 1) shows a single band in the monomer size interval ('m'). The size distribution of PCR products obtained with primers WA11 and WA12 shows additional small fragments (lane 2). The different DNA fragments can be found in Bam H1 digested plasmid DNA (lane 3). ('m' indicates inserts in the monomer size interval; 'pBS' indicates the linearized plasmid DNA.) The sizemarker DNA lane (szm) contains 400 ng of φX174 RF DNA/Hae III digest.

Figure 6:
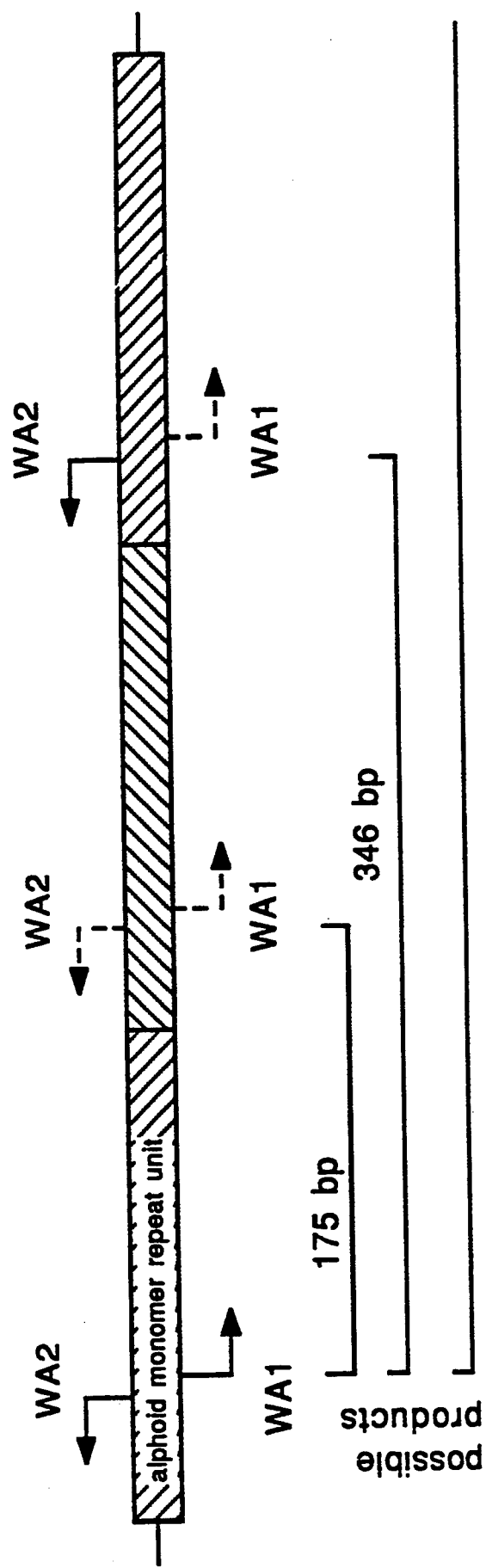

FIG. 6 shows schematically the putative structure of alpha satellite DNA repeats and possible annealing sites of oligonucleotide primers. Arrows indicate the direction of primer extension by DNA polymerase. Shaded areas indicate stretches of alphoid DNA that have higher homology with the alphoid consensus sequence. The expected sizes of primer extension products using primers WA1 and WA2 in a PCR protocol are indicated at the bottom of the figure.

DETAILED DESCRIPTION OF THE INVENTION

The following abbreviations are used herein:

| Abbreviations | |
| --- | --- |
| A- | adenine |
| AB- | antibody |
| AAF- | N-acetoxy-2-acetylaminofluorene |
| AMCA- | 7-amino-4-methylcoumarin-3-acetic acid |
| bcip/npt- | 5-bromo-4-chloro-3-indolylphosphate/nitroblue tetrazolium |
| Buffer A- | Amplification buffer consisting of 10 mM Tris-HCl, pH 8.4 at 20° C.; 1.5 mM MgCl$_2$; 50 mM KCl; 0.2 mM each of dATP dCTP, dGTP and dTTP [all dNTPs from Sigma Chem. Co. (St. Louis, MO USA)] |
| bp- | base pair |
| BRL- | Bethesda Research Laboratories [Gaithersburg, MD (USA)] |
| C- | cytosine |
| °C.- | degrees centigrade |
| DAPI- | 4,6-diamidino-2-phenylindole |
| dATP- | 2'-deoxyadenosine 5'-triphosphate |
| dCTP- | 2'-deoxycytidine 5'-triphosphate |
| dGPT- | 2'-deoxyguanosine 5'-triphosphate |
| dITP- | 2'-deoxyinosine 5'-triphosphate |
| DNA- | deoxyribonucleic acid |
| dNTP- | deoxynucleotide triphosphate |
| dTTP- | 2'-deoxythymidine 5'-triphosphate |
| dUMP- | 2'-deoxyuridine 5'-monophosphate |
| dUTP- | 2'-deoxyuridine 5'-triphosphate |
| EB- | ethidium bromide |
| EDTA- | ethylenediaminetetraacetate |
| FA- | formamide |
| FCM- | flow cytometry |
| FITC- | fluorescein isothiocyanate |
| G- | guanine |

| Abbreviations | |
|---|---|
| g- | gram, gravity |
| HPLC- | high performance liquid chromatography |
| h- | hour |
| IPTG- | isopropylthio-beta-D-galactosidase |
| kb- | kilobase |
| KCl- | potassium chloride |
| LB- | Luria-Bertani |
| M- | molar |
| Mb- | megabase |
| Mg- | milligram |
| min- | minute |
| ml- | milliliter |
| mm- | millimeter |
| mM- | millimole |
| N- | normal concentration |
| ng- | nanogram |
| NP-40- | non-ionic detergent commercially available from Sigma as Nonidet P-40 (St. Louis, MO) |
| nt- | nucleotide |
| pBR- | plasmid cloning vector available from BRL (Gibco/BRL Catalog and Reference Guide) |
| PBS- | phosphate-buffered saline |
| pBS- | Bluescribe plasmid cloning vector |
| pH- | hydrogen ion concentration |
| PCR- | polymerase chain reaction |
| PI- | propidium iodide |
| PN-buffer | mixture of 0.1 M $NaH_2PO_4$ and 0.1 M $Na_2HPO_4$, pH 8; 0.1% NP-40 |
| PNM-buffer | Pn buffer plus 5% nonfat dry milk (centrifuged); 0.02% Na azide |
| RCC- | renal cell carcinoma |
| RT- | room temperature |
| sec- | seconds |
| SSC- | 0.15 M NaCl/0.015 M Na citrate, pH 7 |
| T- | thymine |
| Taq- | Thermus aquaticus |
| TE- | 10 mM Tris-HCl, PH 7.5, 0.5 mM Na-EDTA |
| TR- | Texas Red |
| Tris- | tris (hydroxymethyl) aminomethane |
| ug- | microgram |
| ul- | microliter |
| um- | micrometer |
| w/v- | weight to volume |
| w/w- | weight to weight |
| X-Gal- | 5-bromo-4-chloro-3-indolyl-β-D-galactosidase |

The following references are cited herein:

Baldini et al., *Am. J. Hum. Genet.*, 46: 784–788 (1990);
Baldini and Ward, *Genomics*, 9: 770–774 (1991);
Bauman et al., In: *Flow Cytometrics* (Gray, J. W. ed.) [Academic Press New York (1989)];
Berdize, *Satellite DNA* [Springer-Verlag, Berlin, Heidelberg, New York, Tokyo (1987)];
Brigati et al., *Virology*, 126: 32–50 (1983);
Buckton and Evans, *Methods for the Analysis of Human Chromosome Aberrations* [World Health Organization, Geneva (1973)];
Chamberlain, et al., *Nucl. Acid Res.*, 16: 11141–11156 (1988);
Choo et al., *Genomics*, 7(2): 143–151 (June 1990);
Collins et al., *Genomics*, 11 (4): 997–1006 (December 1991);
Cooke and Hindley, *Nucl. Acids. Res.* 6: 3177–3197 (1979);
Cooke et al., *Clin. Genet.* 30: 485–493 (1986);
Cremer et al., *Hum. Genet.*, 74: 346–352 (1986);
Cremer et al., *Hum Genet.*, 80: 235–246 (1988);
Dahl et. al., *Am. J. Hum. Genet.* 43: 502–510 (1988);
Devilee et al., *Nucl. Acids Res.*, 14: 2059–2073 (1986);
Devilee et al., *Genomics*, 3: 1–7 (1988);
Donlon et al., *Cytogenet. Cell Genet.*, 46: 607 (1987)
Earnshaw et al., *Chromosoma*, 98: 1–12 (1989);
Emmerich et al., *Lab. Invest.*, 61: 235–242 (1989);
Friedman et al., "Screening of lambda gt11 Libraries," In: *PCR Protocols* (Innis et al. eds.) [Academic Press, San Diego, Calif. (USA), pp. 253–258 (1990)];
Frommer et al., *Chromosoma*, 97: 11–18 (1988);
Gahrton et al., *Blood*, 56: 640–647 (1980);
Green and Olson, *PNAS*, 87: 1213–1217 (1990);
Guatelli et al., *PNAS*, 87: 1874–1878 (March 1990);
Gussow and Clackson, *Nucl. Acids Res.*, 17: 4000 (1989);
Harper et al., *Blut*, 48: 33–43 (1981a);
Harper et al., *PNAS*, 78: 4458 (1981b);
Hopman et al., *Histochem*, 89: 307–316 (1988);
Hopman et al., *Am. J. Path.*, 135: 1105–1117 (1989);
Hulsebos et al., *Cytogenet. Cell Genet.*, 47: 144–148 (1988);
Johnson, *Genomics*, 6: 243 (1990);
Johnson and de C. Nogueira Araujo, *J. Immunol. Meth.*, 43: 349–351 (1981);
Jorgensen et al., *J. Mol. Biol.* 187: 185–196 (1986);
Kievits et al., *J. Virol. Methods*, 35 (3): 237–286 (1991);
Knuutila et al., *New Engl. J. Med.*, 314: 865–869 (1986);
Koch et al., *Chromosoma*, 98: 259–265 (1989);
Kohno et al., *Am. J. Hematol.*, 7: 281–291 (1979);
Kunicka et al., *Cancer Res.*, 47: 3942–3947 (1987);
Landegent et al., *Exp. Cell Res.*, 153: 61–72 (1984);
Lewin, B., *Genes* III [John Wiley and Sons, New York (1987)];
Lindquist et al., *Scan J. Haemotol*, 21: 109–114 (1978);
Lizardi et al., *BioTechnology*, 6: 1197–1202 (1988);
Lo et al., *Nucl. Acids Res.*, 16: 8719 (1988);
Lo et al., "Incorporation of biotinylated dUTP", In: *PCR Protocols* (Innis et al. eds.) [Academic Press, San Diego, pp. 113–118 (1990)];
Maniatis et al., *Molecular Cloning: A Laboratory Manual* [Cold Spring Harbor: Cold Spring Harbor Laboratory (1986)];
Manuelidis, *Chromosoma*, 66: 23–32 (1978);
McGuire and Dressier, *J. Natl. Cancer Inst.*, 75: 405–410 (1985);
Meltzer et al., *Nature-Genetics*, 1(1): 24–28 (1992)
Meyne and Moyzis, *Genomics*, 4: 472–478 (1989);
Moroi et al., *PNAS*, 77: 1627–1631 (1980);
Murano et al., *Clin. Genet.*, 39: 68–74 (1991);
Murray and Martin, *Gene*, 57: 255–259 (1987);
Nakahori et al., *Nucl. Acids Res.*, 14: 7569–7580 (1986);
Nakamura et al., *Science*, 235: 1616 (1987);
Nederlof et al., *Cancer Genet. Cytogenet.*, 42: 87–98 (1989);
Nelson et al., *PNAS*, 86: 6686–6690 (1989);
Olsen et al., *Prenat. Diagn.*, 7: 413–417 (1987);
Pinkel et al., "Cytogenetic analysis by in situ hybridization with fluorescently labeled nucleic acid probes. In: *Cold Spring Harbor Symposia on Quantitative Biology*, Vol. LI [Cold Spring Harbor, Cold Spring Harbor Laboratory, pp. 151–157 (1986)];
Pinkel et al., *PNAS*, 85: 9138–9142 (1988);
Poddighe et al., *Cancer Res.*, 51: 1959–1967 (1991);
Puchkova et al., *Hum. Genet.*, 64: 257–262 (1983);
Remvikos et al., *Cytometry*, 9: 612–618 (1988);
Rettig et al., *Somatic Cell Mol. Genet.*, 14: 223–231 (1988);
Saiki et al., *Science*, 235: 1616 (1988a);
Saiki et al., *Science*, 239: 487–491 (1988b);
Sanger et al., *PNAS*, 74: 5463–5467 (1977);
Saunders et al., *Nucl. Acids Res.*, 17: 9028 (1990);
Schwartz et al., *Nucl. Acids Res.*, 18: 1079 (1990);
Shackney et al., *Cytometry*, 11: 94–104 (1990);
Shmookler et al., *J. Mol. Biol.*, 186: 31–41 (1985);

Smidt-Jensen and Lind, *Clinical Genetics*, 32: 133–136 (1987);
Trask et al., *Hum. Genet.* 78: 251–259 (1988);
Trask et al., *Somatic Cell Mol. Genet.*, 17: 117–136 (1991);
Trent, *Breast Cancer Res. Treatm.*, 9: 221–229 (1985)
Van Dekken et al., *Cancer*, 66: 491–497 (1990);
Van Dilla et al., *Bio/Technology* 4: 537–552 (1986);
Vissel and Choo, *Genomics*, 5: 407–414 (1989);
Walker et al., *PNAS*, 89: 392–396 (1992);
Waye and Willard, *Nucl. Acids Res.*, 15: 7549–7569 (1987);
Waye et al., *Nucl. Acids Res.*, 13: 2731–2743 (1985);
Waye et al., *Molec. and Cellular Biol.*, 6: 3156–3165 (1986);
Waye et al., *Chromosoma*, 95: 182–188 (1987a);
Waye et al., *Genomics*, 1: 43–51 (1987b);
Waye and Willard, *Chromosoma*, 97: 475–480 (1989);
Weier and Gray, *DNA* 7: 441–447 (1988);
Weier and Rosette, *Nucl. Acids Res.*, 16: 11836 (1988);
Weier and Rosette, *BioTechniques*, 8: 252–257 (1990);
Weier et al., *J. Histochem. Cytochem.*, 38: 421–426 (1990)
Weier et al., *Hum. Genet.* 87: 489–490 (1991a);
Weier et al., *Chromosoma*, 100: 371–376 (1991b);
Weier et al., *BioTechniques*, 10: 498–505 (1991c);
Willard, *Am. J. Hum. Genet.*, 37: 524–532 (1985);
Willard, *Trends in Genetics*, 6: 410–416 (1990)
Willard and Waye, *Trends in Genet.* 3: 192–198 (1987);
Willard et al., *Nucl. Acids Res.*, 11: 2017–2033 (1983);
Wu and Manuelidis, *J. Mol. Biol.*, 142: 363–386 (1980);
Wyrobek et al., *Mol. Reprod. Devel.*, 27: 200–208 (1990);
Yang et al., *PNAS*, 79: 6593–6597 (1982);
Yoneda et al., *Chromosoma*, 100: 187–192 (1991).
Yurov et al., *Hum. Genet.*, 76: 157–164 (1987);
Zinkowski et al., *Chromosoma*, 94: 243–248 (1986);

The present invention describes probes, and a methods for making them, which are specific for repeat sequences on chromosomes. Although the examples herein are directed to human chromosomes, the methods of this invention can be used to produce repeat sequence probes of high specificity for other species, notably animal species, preferably mammalian including but not limited to guinea pigs, rabbits, mice, rats and hamsters.

Repeat sequences can occur in the genome in multiple copies which range from two to hundreds of thousands of copies. The copies of a repeat sequence may be clustered in one or more locations such as near the centromere, telomere or variable number tandem repeat (VNTR) [Nakamura et al. 1987]. Copies of the repeat sequences may be clustered, or they may be interspersed, that is, distributed on one or more chromosomes or throughout a genome.

Chromatin in metaphase chromosomes, is in a highly condensed state. Certain classes of chromatin may also remain in a somewhat condensed state throughout the cells' cycle. A major part of this condensed chromatin is composed of so-called satellite DNA. Various families of satellite DNA have been described, including those referred to as alpha, beta (also termed the Sau 3A family) and gamma satellites or another group, human satellites I, II, III and IV. A common feature of these satellite DNA structures is that they are composed of small repeated units, for example, the alpha satellite repeat unit in humans is approximately 171 bp in length. Representative clustered repeat sequences are alpha satellites, beta satellites; satellites I, II, III and IV; and the 39 bp repeat that maps to 1p36.

Primer Sequences

Primer sequences are selected from identified DNA sequence regions for their capacity to bind selected highly repeated sequences, such as repeats in satellite DNA. Appropriate oligonucleotide primer sequences are selected and then synthesized by automated chemical synthesis methods. One or more bases in the primer sequence may be modified to make a primer which has related, but different binding activity.

Typically, probe primer sequences are chosen which not only flank the desired probe sequence, but are included within the probe sequence itself in order to avoid the requirement for separation. In one preferred embodiment of the invention, the binding sites of one set of degenerate primers are within a distance of from about 20 bp to about 5 kb of the binding sites of said second set of primers. Primers may range from 8 to 100 bp in length, more preferably 20–30 bp. When very small primers are selected, annealing is accomplished at very low temperatures, often as low as 4° C. The most useful primers are those which bind only to areas where the selected repeat sequences will be primed to avoid obtaining undesired sequences in the amplification products.

The appropriate probe oligonucleotide primer sequences are selected by reviewing large maps of repetitive sequences in the target chromosome, and selecting, by means of the above criteria, the most likely oligonucleotide primer sequences for a proposed probe from within those sequence maps. The most useful probe primer sequence is selected by balancing the appropriate binding factors required to enable synthesis with the target binding specificity required to bind and subsequently visualize the probe.

Primers for the probes for the repeat sequences of any repeat unit, such as centromeric repeat sequences, are made by selecting degenerate oligonucleotide primers which are homologous to two regions near the extent of the repeat sequences. The appropriate primer for the desired repeat sequence probe is made by selecting and making a set of degenerate oligonucleotide primers which contain a variety of different nucleotide sequences, each of which is slightly less than homologous to a specific stretch of nucleic acid of a known repeat sequence on the target nucleic acid. They may differ by one or more bases from the binding sequence on the target DNA. For example, the degeneracy of the primer sequence, introduced by the chemical oligonucleotide synthesis, is eight to 16-fold, with a 12-fold degeneracy preferred, in particular. Additional restriction enzyme recognition sites may be added to the primer to facilitate further molecular cloning. The sequences of oligonucleotide primers used in the examples and other nondegenerate primers are shown in Table I.

TABLE 1

| Synthetic oligonucleotides used in the examples | |
|---|---|
| WA1[2)] [SEQ ID NO: 1] | GAAGCTTA($^A/_T$)($^C/_G$)T($^C/_A$)ACAGAGTT($^G/_T$)AA |
| WA2[2)] [SEQ ID NO: 2] | GCTGCAGATC($^A/_C$)C($^A/_C$)AAG($^A/_T/_C$)AGTTTC |
| WA11[2)] [SEQ ID NO: 3] | CCC GGA TCC CTG CAG AAG CTT A(A/T)(C/G)T(C/A) ACA |

TABLE 1-continued

Synthetic oligonucleotides used in the examples

| | |
|---|---|
| WA12[2] [SEQ ID NO: 4] | CCC GGA TCC AAG CTT CTG AGA TC (A/C)C(A/C) AA |
| WGS1 [SEQ ID NO: 5] | CCC AAG CTT GAA ATG TCC ACT |
| WGS2 [SEQ ID NO: 6] | CCC AAG CTT TTT CTT GCC ATA |
| WBS2 [SEQ ID NO: 7] | CTC GGA ATT AAC CCT CAC TAA AGG |
| WBS4 [SEQ ID NO: 8] | GAA TTG TAA TAC GAC TCA CTA TAG |
| WXR1 [SEQ ID NO: 9] | TCG AAA CGG GTA TAT GCT CAC GTA AAA |
| WXR2 [SEQ ID NO: 10] | AAG ACA GTT TCA AAA CTG CTC CAT CAA |
| W21R1 [SEQ ID NO: 11] | GGA TAG CTT AAC GAT TTC GTT GGA AAC |
| W21R2 [SEQ ID NO: 12] | CAA ACG TGC TCA AAG TAA GGG AAT G |
| WYR9 [SEQ ID NO: 13] | ATG GAA TTG AAT GGA ACG GAA TAG AGT |
| WYR10 [SEQ ID NO: 14] | CGA TTC CAT TCA ATT CGA GAC CAT TCT |

[1] All oligonucleotides are listed from 5' to 3'.
[2] Degenerate primer.

Probes for the repeat sequences of human centromeres can be made by selecting degenerate oligonucleotide primers which are homologous to two regions of the 171 bp alpha satellite repeat sequence. That repeat sequence is conserved in all human chromosomes. Specifically, in a preferred example, two primers were produced which bind to the alpha satellite repeat consensus sequence at bp positions 37-52 and 10-26. The consensus sequence for alpha satellite DNA was published by Waye and Willard (1987).

The selected primer sequences are termed primers WA1 and WA2, respectively. The sequences are the 16-fold and the 12-fold degenerate oligonucleotide primers (23 mers) and are:

WA1 [SEQ ID NO: 1]
5'-GAAGCTTA(A/T)(C/G)T(-C/A)ACAGAGTT(G/T)AA-3'; and

WA2 [SEQ ID NO: 2]
5'-GCTGCAGATC(A/C)C(A/C)AAG(A/T/-C)AGTTTC-3'.

Each primer carries a 6-base pair restriction enzyme recognition site (underlined bases) to facilitate molecular cloning of the PCR products. The primer WA1 carries a 5' Hind III site recognition sequence, and the WA2 primer carries a Pst 1 recognition sequence. The extra base on the 5'-ends was added during automated primer synthesis to ensure proper reproduction of the restriction sites by the Thermus Aquaticus (Taq) DNA polymerase, a thermostable enzyme which lacks any proof-reading capability.

The primers are placed so that the 5'-ends face each other when annealed to the genomic DNA template. The minimal product size expected is 175 bp, based on the distance between the annealing sites (FIG. 6). During amplification of longer products, multiple 170 bp repeat sequences, may occur between primer and annealing sites when the individual monomeric repeat units have a lower degree of homology with the consensus sequence, so that the primers can not anneal in each repeat monomer. In this example, the primer annealing sites are separated by one or more repeat units. As such, the DNA segments amplified contain DNA segments of 175 bp size plus one or more multiples of the 171 bp repeat unit.

The primer sequences listed herein in Table I may not be suitable for amplifying all naturally occurring alphoid sequences. For example, alphoid sequences derived from the human Y chromosome are not well amplified by primers WA1 and WA2 or by WA11 and WA12. However, the degeneracy of the primers introduces a maximum flexibility in using the amplification scheme, and ones of ordinary skill in the art would know how to prepare various primers according to this invention for different chromosomes, as for example, the Y chromosome.

As indicated by the sequence analyses of the clones pBS609-51 and -52 as discussed infra in Example 2 and shown in Table II, different primer sequences are involved in the probe amplification process, and the primer sequences differ from the consensus sequence. Different primer sequences from the pool of primer sequences represented by WA1 and WA2 may anneal to individual stretches of template DNA as schematically represented in FIG. 6; thus, the complexity of the amplification products is increased.

Further evidence of the high complexity of the probes produced according to this invention is the discrete size intervals found in gel electrophoretic separation. Monomeric fragments of approximately 175 bp were the smallest predicted amplification products. They were observed in relatively high frequency among the amplification products for chromosomes 8 and 10 as shown in Examples 1 and 2. Those results may reflect the presence of rather large domains of alphoid DNA with high degree of homology with the alphoid consensus sequence. At a lower frequency were found DNA fragments of higher molecular weight that were amplified in the initial reaction indicating that consensus DNA, and thus, the primer annealing sites, flank more diverse satellite repeats. In addition, heterogeneously sized DNA fragments were found to be amplified in the examples; the origin and nature of those fragments are yet to be investigated.

The size distribution of the chromosome 10 derived amplification products shown in Example 2 is very similar to that observed when chromosome 8-specific template DNA was used as shown in Example 1. In both examples, the biotinylated probe showed significant crosshybridization that can be blocked by the addition of unlabeled total human alphoid DNA and/or with total genomic DNA. Cot 1, genomic DNA enriched in repetitive sequences, can also be used. As shown in Example 1, separation of the chromosome 8-specific amplification products into three different sizes and their hybridization to metaphase spreads and interphase nucleic indicate that the crosshybridization was mostly due to the monomeric fraction whereas the longer DNA fragments showed higher specificity for the target chromosome 8.

Arbitrarily Selected Repeat Probes

If annealing sites are part of an inverted repeat, the reaction may be performed with one primer. When the annealing sites have the same orientation along the chromosome (i.e. pter to qter direction), one or more pairs of oligonucleotide primers can be used. The primer molecules can be complementary to each other, as long as annealing to each other during one PCR cycle does not interfere with annealing of the primer molecules during subsequent cycles. Oligonucleotides that bind to sequences as small as 4–10 bp in length can be used as primers.

A preferred primer of this invention for arbitrarily priming is termed Jun1 which has the following 29 nucleotides:

5'-CCCAAGCTTGCATGCGAATTCXXXX-CAGG-3' [SEQ ID NO: 15]

wherein each X stands for any of the 4 DNA bases—A, C, G or T. Therefore, said primer has 256 possible combinations by changing the 4X positions (4×4×4×4=256). Those X positions are 5' to the 4 base recognition sequence that was found to be conserved at spliced junctions. At the 5' end of Jun1 is the triplet sequence CCC which serves as a C/G clamp to keep the hybridized strands together. The next 18 nucleotides provide a number of different restriction enzyme recognition sites.

The Jun1 primer can be used in combination with human genomic DNA or chromosome-specific DNA, as for example, flow-sorted chromosomes, to amplify chromosome-specific repeated DNA. When the Jun1 primer is used, the 39 bp repeat that maps to 1p36 is preferentially amplified.

Synthesis of the Probe

The synthesis of the probe may be accomplished by conventional polymerase chain reaction (PCR) process. The mechanics of PCR are explained in Saiki et al., *Science* 230: 1350 (1985) and U.S. Pat. Nos. 4,683,195 and 4,683,202 (both issued Jul. 28, 1987) and 4,800,159 (issued Jan. 24, 1989). A PCR adapter-linker method is explained in Saunders et al. (1990); Johnson (1990) and PCT 90/00434 (published Aug. 9, 1990). Another PCR method employing a mixture of primers is described in Meltzer et al., "Generation of Region Specific Probes by Chromosome Microdissection: A Novel Approach to Identify Cryptic Chromosomal Rearrangements," *Nature—Genetics,* 1 (1): 24–28 (April 1992).

Once the methods of this invention employing PCR using degenerate primers has separated the repeat sequence probe sequences from the genomic DNA, many different methods can be used to prepare large quantities of the probes for screening, sequencing and/or use in in situ hybridization experiments. For example, the PCR amplification products can be further amplified by PCR processes and/or molecularly cloned in a variety of vectors as illustrated in Example 2.

It should be noted in the cloning strategy that oligonucleotides WA1 and WA2 are not optimal to prime probe synthesis from clonal templates, because only a fraction of the primers can be used for probe production due to the sequence degeneracy. Primers that anneal to flanking vector sequences are advantageous, because each primer can be extended into a probe molecule, and a single pair of vector primers can be used to amplify different kinds of inserts, i.e., different probe molecules that were cloned into the same vector. Once the insert has been sequenced, one can synthesize nondegenerate primers that match the 5' ends of the insert. Then, the two pairs of primers can be used as nested sets for improved specificity (Lo et al. 1990; Weier et al. 1991c) in a step reaction similar to the probe synthesis scheme described above. A collection of chromosome-specific sequences selected for specificity among other parameters provides a brighter and stronger hybridization signal than a single chromosome-specific probe as the target sites are more extensive. Automated programmable PCR methods may be used for large scale probe synthesis such as that using thermostable DNA polymerase which was described by Weier and Gray (1988).

Newer techniques using the Q-beta replicase system [Lizardi et al. 1988] or ligase chain reaction, as commercialized by BioTechnica International Inc, [Cambridge Mass. (USA)], could be used to make copies of the desired probe or probes. Further, an isothermal in vitro amplification of those DNA sequences using a restriction enzyme DNA polymerase system could be used as described in Walker et al. (1992), Guatelli et al. (1990), and Kievits et al. (1991).

Reagent quantities of probe sequences can also be produced by cloning with the use of any one of a number of appropriate vectors, or reproduced by other means when there is a need for multiple copies to be used as probes. Promoter sequences or other useful sequences can be added to the probes to improve replication yield. In the cloning strategy, preferred restriction enzymes are those that are 6-cutters rather than 4-cutters; it is preferred that the enzymes cut at the ends and not at the middle of the probes. Preferred exemplary enzymes are Bam H1, Pst 1 and Hind III.

Template DNA

Limiting the complexity of the template DNA is important for chromosome-specificity of the amplification products prepared according to this invention. Preferably, for the generation of probes of this invention, chromosomes isolated by flow sorting are used as the template DNA. The chromosome-specific DNA may also be isolated from a hybrid cell, or be isolated by microdissection, by density gradients or by other means. Further, the chromosome-specific template DNA can be chromosome-specific libraries. An example of a hybrid cell containing a particular chromosome or portion thereof of one species would be the use of a human X hamster radiation hybrid that contained the centromeric region of chromosome 10 as the only human DNA as the template DNA. Amplification products from such isolated DNA show preferential binding to chromosome 10 in in situ hybridization experiments.

Labeling of Probes

The probes of this invention can be labeled during the PCR amplification in the presence of appropriately modified dNTPs, or they can be labeled after completion of the PCR reaction by chemical or enzymatic modification of the PCR products. Any of the various labeling techniques, direct or indirect, may be used to label probes, including but not limited to fluorescent chemicals, radioactive materials, chemical haptens, or enzymatic modifiers. More than one label can be used. Preferred modified dNTPs include but are not limited to biotin-11-dUTP; digoxigenin-11-dUTP; biotin derivatives of dATP; fluoresceinated-dUTP; rhodamine labeled derivatives of dUTP; rhodamin labeled derivatives of dCTP; hydroxy coumarin-labeled derivatives of dUTP; and resorufin-11-2'-dUTP. Preferred labels include but are not limited to AAF, sulfur and mercury.

The staining intensity achieved using the probes may be amplified with a variety of systems, including but not limited to fluorochrome conjugated avidin and/or labeled antibodies. Similarly, other detection schemes such as labeling of probe molecules with enzymes, sulfur or mercury may be applied in order to suit special experimental conditions. DNA can be counterstained with DNA-specific dyes, including but not limited to DAPI, that fluoresce in different wavelength intervals dependent on the selected scheme for visualization of bound probe molecules.

The degenerate alpha satellite probes (das probes) appear to generate higher signal intensities than other available cloned alpha satellite probes. Since the probe covers a relatively large target area and is intensely labeled, visualization of the probe requires few amplification steps. The biotinylated probe requires only a single conjugation step, using avidin-FITC, which eliminates laborious signal amplification steps that are required by other visualization techniques for centromeric alpha DNA. While the degenerate alpha satellite probe may contain small non-alpha satellite repeat sequences interspersed within the centromeric alpha DNA [Jabs and Persico 1989], the probe is primarily composed of alpha satellite monomer and high-order repeats, as indicated by gel electrophoresis.

In Situ Hybridization

As indicated in Examples 1 and 2 below, the probes of this invention can be used for in situ hybridization to metaphase spreads, interphase nuclei and/or tissue sections. The interphase nuclei can be from germ line cells and/or somatic cells. The chromosomal material of micronuclei can also be a target of appropriately sized probes of this invention. Modifications of standard hybridization protocols as detailed in Pinkel et al. 1988 are used.

In Examples 1 and 2, it is shown that centromeric repeated DNA can be selectively amplified using a pair of degenerate alpha satellite consensus primers. PCR reproduces naturally occurring variations in the base sequences between primer annealing sites by using oligonucleotide primers that anneal in the most conserved parts of the alphoid monomer repeat. The resulting probe DNA is a heterogeneous mixture of DNA fragments in different size ranges with a variety of nucleotide sequences. The degeneracy of the PCR-generated probe DNA may be advantageous during in situ hybridization compared to the use of conventional clonal DNA probes, because it allows deposition of a very dense array of probes along the chromosomal target.

As indicated in Example 1, the alphoid probe DNA obtained by amplification using isolated chromosomes 8 is composed of at least two major fractions that differ in specificity of hybridization to target chromosomes. The crosshybridization is apparently caused mostly by the monomeric fragments. That crosshybridization can be minimized by the addition of unlabeled total human alphoid DNA to the hybridization mixture. The dimeric and high molecular weight fractions of the chromosome 8-specific alphoid DNA bind with sufficient specificity during hybridization to allow identification of chromosome 8 heterochromatin in interphase nuclei.

Similarly, crosshybridization with the chromosome 10-specific alphoid DNA was reduced by the addition of blocking DNA, either total human alphoid DNA and/or total human genomic DNA. Cot 1 DNA can also be used. The preferred ratio (w/w) for human alphoid blocking DNA to labeled probe of this invention is from about 2:1 to about 5:1. The preferred ratio (w/w) of total human genomic DNA to labeled probe of this invention is from about 10:1 to about 30:1, preferably about 25:1. The blocking DNA is used to inhibit less specific elements of the probe from binding.

Molecular Cloning

The PCR methods of this invention using degenerate primers as indicated above produce a heterogeneous mixture of probes, some of which are more or less chromosome-specific. As indicated immediately above, blocking DNA is used to inhibit the less specific elements of the mixture from binding. Thus, the addition of the blocking DNA creates a chromosome-specific staining reagent from the heterogenous mixture.

As exemplified in Example 2, highly specific repeat sequence probes can be prepared by screening the heterogeneous mixture for highly specific probe elements. In a representative screening method, the probe elements can be molecularly cloned, and clones selected first that contain inserts in an appropriate size range. The appropriately sized elements are then labeled and screened by in situ hybridization experiments for chromosome-specificity. Also clones can be selected for those containing inserts that have highly repeated DNA; highly repeated sequences have more target sites and deliver stronger hybridization signals. There can be many variations of the screening protocol, but that presented in Example 2 is one preferred screening method.

Once a clone has been found to contain a highly specific repeat sequence, for example, as were the chromosome 10-specific clones pBS609-51 and pBS609-52, such a clone is a preferred template for PCR based probe production. Restriction fragments cloned from genomic DNA often contain less specific DNA among their kilo basepairs (kb) of insert DNA, that can cause crosshybridization with other chromosomes and thus lower the signal-to-noise ratio. Furthermore, large DNA inserts have to be broken up into smaller fragments in the order of 300–400 bp or smaller to allow efficient diffusion into interphase cell nuclei, metaphase chromosomes or the densely packed chromatin in sperm nuclei. Probes generated from monomeric or dimeric alphoid inserts by PCR do not need to be broken into smaller pieces. In addition, there is no need to remove unincorporated dNTPs, so that PCR products can be directly applied for in situ hybridization.

Another useful aspect of probe generation by PCR from clonal templates is the fact that primers can be designed to incorporate some parts of the vector sequence into the probe (Lo et al. 1988; Weier and Rosette 1988). The non-homologous vector tail on the 5'-end of the probe molecules does, in most cases, not interfere with probe annealing during the hybridization (Frommer et al. 1988; Weier et al. 1991c), but might virtually enlarge the hybridization target and enhance signal intensity by binding an increased number of reporter molecules. Some preferred vectors include Bluescribe plasmids and more generally pUC derived plasmids. Preferred primers include but are not limited to WBS2, WBS4 (Table I), M13 forward and reverse sequencing primers, and primers that bind to T3 and T7 RNA polymerase promoters.

The following examples are for purposes of illustration only and are not intended to limit the scope of the invention in any way.

EXAMPLES

Example 1

Probe for human chromosome 8-specific alpha satellite DNA

A centromere specific probe, which is specific for chromosome 8, was made by using degenerate PCR primers for two conserved regions of the 171 bp alpha satellite monomer to amplify alpha satellite DNA from sorter-purified chromosome 8 DNA template. Degenerate oligonucleotide primers, WA1 and WA2, homologous to the alpha satellite consensus sequence were synthesized, using phosphoramidite chemistry on a DNA synthesizer [Applied Biosystems, Foster City, Calif. (USA), model 380B]. Synthesis and further purification of the oligonucleotides by $C_{18}$ reverse phase chromatography and HPLC were performed according to the specifications of the manufacturer [Waters Chromatography, Milford, Mass. (USA)].

a. Amplification of Total Human Alphoid DNA

Approximately 5000 lymphocytes isolated from peripheral blood of a male donor were used as DNA template. The reaction buffer consisted of 5 units of Taq DNA polymerase (5 units/ul; BRL) mixed with 200 ul amplification Buffer A and the two primers (WA1 and WA1; 1.2 uM each). Mineral oil [100 ul, Squibb, Princeton, N.J. (USA)] was layered on top of the reaction mix to prevent evaporation during PCR. DNA amplification was performed during 25 cycles using an automated thermal cycling system [Weier and Gray 1988]. Each cycle began with a thermal denaturation step of 120 seconds at 94° C. (180 seconds for the initial denaturation). Primer annealing during the second step of each cycle was performed at 45° C. for 90 seconds. The temperature was then increased slowly (7° C./min) to 72° C. The cycle was completed by holding that temperature for 120 seconds for primer extension. Amplification of alpha satellite DNA was confirmed visually by electrophoresis of 5 ul aliquots of the PCR reaction on 4% agarose gels (BRL) in 40 mM Tris-acetate, 1 mM EDTA, pH 8.0 containing 0.5 ug/ml EB. The concentration of double-stranded DNA in the reaction was determined to be 229 ug/ml by Hoechst 33258 fluorescence using a TK 100 fluorometer [Hoefer Scientific, San Francisco, Calif. (USA)].

b. Amplification of Chromosome 8 Alphoid DNA

Approximately 2000 chromosomes from a flow sorted chromosome 8 preparation, at a concentration of approximately 330 chromosomes per ul, were used as DNA template for each PCR amplification. The reaction buffer consisted of 5 units of Taq DNA polymerase (BRL) mixed with 200 ul amplification Buffer A containing the two oligonucleotide primers WA1 and WA2 (1.2 uM each). Mineral oil was layered on top of the mix, and DNA amplification was performed during 40 cycles following the described temperature changes. Amplification of alpha satellite DNA fragments was confirmed by gel electrophoresis of 10 ul aliquots of the final PCR reaction in either 1.7% or 4% agarose. DNA fragment bands that appeared on the 4% agarose gel were excised and DNA was isolated using a commercially available kit [Geneclean, BIO101, San Diego, Calif. (USA)]. The DNA fragments were separated into three size classes: monomeric fragments with an estimated size of 175 bp, dimeric fragments that appeared at approximately 346 bp, and high molecular weight DNA fragments in the size range from 500 bp to several kilobase pairs (kb). The DNA was resuspended in 20 ul water after complete removal of agarose and high salt solutions.

c. Labeling of Chromosome 8-specific Alpha Satellite DNA

A two microliter aliquot of the unfractionated PCR solution from the 40 cycle chromosome 8-amplification was resuspended in 200 ul of biotinylation Buffer A wherein the dTTP was replaced with Biotin-11-dUTP (Sigma) and 1.2 uM of each primer WA1 and WA2, with 8 units of Taq polymerase. The tube was capped with 100 ul of mineral oil; the alpha satellite DNA was amplified and biotinylated for an additional 20 cycles.

Aliquots of 4 ul were taken from each of the three size-fractionated PCR products resuspended in 200 ul biotinylation buffer containing 8 units of Taq polymerase as above and amplified for an additional 20 cycles. The concentration of labeled probe DNA generated from unfractionated products was 21 ug/ml according to fluorometric analysis after completion of PCR. Concentrations of biotinylated DNAs after gel electrophoretic separation and extraction were determined to be 28 ug/ml for the monomeric fraction, 20 ug/ml for the dimeric fraction, and 44 ug/ml for the high molecular weight fraction. Labeled probe DNAs were stored without further purification at −18° C. until used for in situ hybridization.

d. In situ Hybridization

Metaphase spreads were made from phytohemagglutinin [PHA, Gibco, Grand Island, N.Y. (USA)] stimulated short-term lymphocyte cultures according to the procedure described by Harper et al. (1981b). Cell cultures were synchronized with methotrexate ($10^{-5}$M, Sigma) and acetic acid/methanol (1:3) fixed metaphase spreads were prepared as described elsewhere [Weier et al. 1990]. Slides were stored under dry nitrogen in sealed plastic bags at −20° C. until used. Test samples included mononuclear cells that were isolated from bone marrow samples from patients under anti-proliferative therapy.

Biotinylated probe DNAs (approximately 20 ng) and selected amounts of unlabeled human genomic alpha satellite DNA were added without purification to 8 ul of the hybridization mix described by Pinkel et al. 1986. Water was added to 10 ul so that the final concentration in the hybridization mix was 55% formamide [IBI, New Haven, Conn. (USA)], 10% dextran sulfate, 1 ug/ul herring sperm DNA, 2×SSC (2×SSC is 0.3M NaCl, 0.03M Na citrate), at pH 7.0. DNA in the hybridization mix was denatured at 72° C. for 5 min. After chilling on ice, the mix was added to the slides that were denatured for 4 min. at 72° C. in 70% formamide, 2×SSC, pH 7.0, covered by a 22 mm by 22 mm coverslip and hybridized overnight at 37° C. The slides were then washed in 50% formamide, 2×SSC, pH 7.0 at 42° C. for 15 min., followed by 2 washes of 15 min. each, in PN buffer at 37° C. Biotinylated probe was detected with a 20 min. incubation at room temperature in avidin-FITC [5 ug/ml, Vector Laboratories, Burlingame, Calif. (USA)], in PN buffer plus 5% non-fat dry milk and 0.02% sodium azide). Excess avidin-FITC was removed by washes in two changes of PN buffer at room temperature, and the DNA was counterstained with PI [Sigma], used at a concentration of either 0.2 ug/ml or 1 ug/ml in antifade solution [Johnson and de C. Nogueira Araujo 1981] or with DAPI [Calbiochem, La Jolla, Calif. (USA)] for metaphase chromosome identification.

In some spreads, the PCR-generated repeat probe was hybridized in combination with the chromosome 8-specific DNA library pBS8 as described in Pinkel et al. (1988) to facilitate identification of chromosome 8.

Results

Gel electrophoresis of unlabeled chromosome 8 PCR products revealed strong bands at approximately 175 bp and 346 bp, indicating the successful amplification of alphoid monomer and dimer sequences. In addition, higher molecular weight DNA fragments were generated.

Figure 1A:
FIG. 1 shows in situ hybridization of the degenerate chromosome 8 alphoid probe DNA in the presence of different concentrations of unlabeled alpha satellite DNA. Probe detection was accomplished using probe labeled with avidin-FITC; chromosomal DNA was counterstained with PI. The photomicrographs show (a) chromosome 8 probe hybridization, in the presence of no blocking DNA; (b) unlabeled total human alphoid DNA and chromosome 8 probe DNA at a ratio of 2:1; and (c) unlabeled total human alphoid DNA and chromosome 8 probe DNA at a ratio of 5:1 (Magnification=1200×).

In situ hybridization of biotinylated probe DNA that was generated by direct biotinylation of chromosome 8 PCR products containing monomeric, dimeric and high molecular weight DNA fragments to normal metaphase spreads in the absence of blocking DNA showed strong labeling of the centromeric regions on numerous chromosomes (FIG. 1a). Interphase cell nucleic typically showed 10 to 20 strongly labeled hybridization domains (FIG. 1a).

Figure 1B:
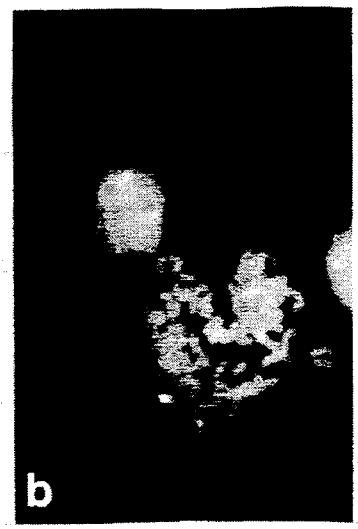
Figure 1C:
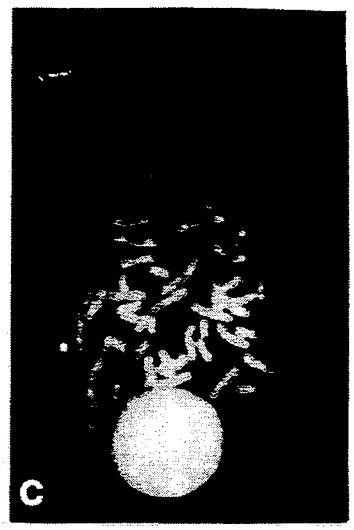

When the unfractionated probe DNA was hybridized in the presence of unlabeled human alphoid DNA, the intensity of the hybridization signal on chromosome 8 decreased only slightly compared to the hybridizations without the blocking DNA while hybridization to the other chromosomes was drastically reduced (FIG. 1b, c). Addition of 0.2 ul blocking DNA to the mix, i.e., ratio of two of blocking DNA to one of biotinylated probe DNA, reduced crosshybridization significantly so that the target chromosomes 8 could easily be identified by their brightly labeled centromeric region (FIG. 1b). By increasing the ratio of blocking to probe DNA to five to one, the crosshybridization was further reduced without compromising signal intensities on the target chromosomes (FIG. 1c).

Figure 2A:
FIG. 2 shows hybridization of size-selected chromosome 8-specific alphoid probe DNA. Probe DNA comprised of alpha satellite monomers shows relatively unspecific binding (a). The fractions of probe DNA containing alpha satellite dimers (b) or high-order repeat units (c) bind with higher specificity to the human number 8 chromosomes (Magnification=1200×).
Figure 2B:
Figure 2C:

The results of in situ hybridization experiments using probe DNA molecules generated by primer-directed in vitro DNA amplification with size-selected PCR products as templates are summarized in FIG. 2. The monomeric fraction exhibited high levels of crosshybridization with nontarget chormosomes (FIG. 2a). Dimeric fragments and high molecular weight fragments, on the other hand, bound preferentially to the chromosomes 8 in metaphase spreads, and two clear hybridization domains were visible in interphase cell nuclei (FIG. 2b, c). In the absence of blocking DNA, the dimeric and high molecular weight fragments showed some crosshybridization with nontarget chromosomes. Such crosshybridization was reduced substantially by the addition of unlabeled total human alphoid DNA.

Microscopy was performed on a Zeiss STANDARD fluorescence microscope (Zeiss, Oberkochen, FRG) equipped with a Plan-Neofluar 63x/1.20 Oil objective using the epi-illumination filter set for FITC (Omega Optical, Brattleboro, Vt.). Photographs were recorded on Kodak Ektachrome 400 film.

Figure 3:
FIG. 3 shows hybridization of the degenerate chromosome 8-specific alphoid probe DNA with bone marrow cells from a CML patient with a tumor cell karyotype of 47,XY,+8. Normal cell nuclei show two domains of bound probe DNAs. Arrowheads point to leukemic cells with three domains of chromosome 8-specific alpha satellite DNA (Magnification=1200×)

A competitive hybridization regimen using unfractionated alpha satellite DNA was used for determination of the number of chromosomes 8 in bone marrow cells from CML (chronic myeloid leukemia) patients under therapy. Trisomy of chromosome number 8 is observed in cases of CML. A typical hybridization to cell samples from a CML patient with a tumor cell karyotype of 47,XY,+8 is shown in FIG. 3. Most cells exhibited either two or three bright spots representing domains of chromosome 8-specific alpha satellite DNA. The relative fraction of karyotypically abnormal cells could rapidly be assessed by counting cells with three domains.

Example 2

Probe for Human Chromosome 10-specific Alpha Satellite DNA a. Oligonucleotide primers Oligonucleotide primers—WA1, WA2, WBS2 and WBS4—homologous to parts of the alpha satellite consensus sequence [Waye and Willard 1987] or the cloning vector pBS were synthesized and purified as indicated in Example 1. The sequences of the oligonucleotide primers including their degenerate positions are shown in Table I. Primers WA11 and WA12 were deprotected by overnight incubation in 2N $NH_3$. The primers were then lyophilized, resuspended in water and ethanol precipitated [Maniatis et al. 1986]. All primers were prepared as 30 uM stock solutions in water and stored at $-20°$ C.

The degenerate alpha satellite primers WA1, WA2, WA11, and WA12 carry non-homologous bases to facilitate molecular cloning of PCR products. Primers WA1 and WA2 carry a 5' Hind III and Pst 1 recognition sequence, respectively. WA11 and WA12 carry short polylinker sequences that represent from 5' to 3' restriction enzyme recognition sites for Bam H1, Pst 1 and Hind III or Bam H1, Hind III and Pst 1, respectively. One or three extra bases were added during primer synthesis on the 5'-ends of WA1 and WA2 or WA11 and WA12, respectively, to ensure proper reproduction of the restriction sites by Taq DNA polymerase during PCR and subsequent digestion. The primers WBS2 and WBS4 anneal specifically to pBS-DNA sequences flanking the multicloning site [Weier and Rosette 1988 and 1990].

b. Amplification of chromosome 10-specific alpha satellite DNA

Approximately 2,000 human chromosomes 10, isolated by flow sorting from the human X hamster cell line R342-A4 [Trask et al. 1991] were used as DNA template in the initial reaction. The reaction buffer consisted of 5 units of Taq DNA polymerase mixed with 200 ul amplification buffer [10 mM Tris-HCl, pH 8.4 at 20° C., 1.5 mM $MgCl_2$, 50 mM KCl], 0.2 mM each dATP, dCTP, dGTP and dTTP, and 1.2 uM each of the primers WA1 and WA2, as described previously. Mineral oil [100 ul, Squibb, Princeton, N.J. (USA)] was layered on top of the reaction mix to prevent evaporation during PCR. DNA amplification was performed during 45 cycles using a Perkin Elmer Cetus Thermal Cycler [Norwalk, Conn. (USA)]. Each cycle included a denaturation step of 120 sec at 94° C. (180 sec. for the initial denaturation), primer annealing at 53° C. for 60 sec. and primer extension for 120 sec at 72° C. Organic and aqueous phases were inverted in the reaction tube by addition of 1.5 volumes of chloroform, and PCR products were transferred to a clean tube. Amplification of alpha satellite DNA was confirmed visually by electrophoresis of a 10 ul aliquot of the PCR reaction in 4% agarose in 40 mM Tris-acetate, 1 mM EDTA, pH 8.0 containing 0.5 ug/ml EB [Maniatis et al. 1986]. The concentration of double stranded DNA in the reaction was determined by Hoechst 33258 fluorescence using a TK 100 fluorometer according to the manufacturer's protocol [Hoefer Scientific, San Francisco, Calif. (USA)].

Gel electrophoresis of unlabeled chromosome 10-specific PCR products from the initial amplification reaction using primers WA1 and WA2 revealed a strong band at approximately 175 bp indicating the successful amplification of the alphoid monomer sequences (FIG. 5, lane 1). Higher molecular weight DNA fragments were generated with much lower efficiency and appeared as a band at approximately 346 bp with an underlying smear of high molecular weight DNA when larger amounts of PCR products were loaded on the gel (data not shown). Separation of the products on 1.8% agarose showed that the background of heterogeneously sized DNA fragments in the range of 600 bp to 20 kb.

c. Labeling of Chromosome 10-specific alphoid DNA

A four microliter aliquot of the PCR solution from the initial reaction was resuspended in 200 ul of biotinylation Buffer A wherein dTTP is replaced with Biotin-11-dUTP, and there is 1.2 uM of each primer WA1 and WA2 and 8 units of Taq. The mix was overlaid with 100 ul of mineral oil and alphoid DNA was amplified and biotinylated for an additional 20 cycles. Mineral oil was removed after addition of chloroform, and labeled probe DNA was stored without further purification at minus 20° C. until used for in situ hybridization.

Aliquots of 200 ul from the initial PCR reactions were labeled with AAF with minor modifications of the procedure published by Landegent et al. (1984) as described in Weier et al. (1991b). After the reaction, DNA was extracted three times with phenol/chloroform/isoamyl alcohol [Maniatis et al. 1986] and then ether-extracted twice at room temperature. DNA was then precipitated in 2.5 volumes of ethanol, 0.1M Na acetate, dried and resuspended in 500 ul 10 mM Tris-HCl, pH 8.0, 1 mM EDTA.

Labeling of PCR products with digoxigenin was performed in a manner similar to the described biotinylation reaction, except that the labeling buffer contained a mixture of digoxigenin and dTTP (0.16 mM and 0.04 mM, respectively) in place of the Biotin-11-dUTP.

d. Synthesis of alphoid Blocking DNA

Unlabeled total human alphoid DNA was synthesized from male human genomic DNA as described elsewhere [Weier et al. 1991b]. Briefly, 200 ng of isolated genomic DNA were mixed with 100 ul amplification mix containinig WA1 and WA2 as described above. PCR was performed for 30 cycles, and the concentration of double stranded DNA was determined by fluorometry. Human placental DNA was prepared for use as a blocking agent by sonication of the supplied DNA until the average size was approximately 300–400 bp as judged by agarose gel electrophoresis.

e. Sample Preparation

Metaphase spreads were made from phytohemagglutinin-stimulated short-term lymphocyte cultures according to the procedure described by Harper et al. 1981b. Acetic acid/methanol (1:3, Carnoy's fixative) fixed metaphase spreads were prepared as described elsewhere [Weier et al. 1990]. Slides were stored under dry nitrogen in sealed plastic bags at −20° C. until used. Cellular and chromosomal DNA was thermally denatured prior to application of the probe mixtures by incubating the slides for 4 min. at 74° C. in 70% formamide, 2×SSC, pH 7.0. The slides were then dehydrated in a 70, 90, and 100% ethanol series and briefly air dried at room temperature.

Samples of kidney tissues were obtained from patients with renal cell carcinoma (RCC) after surgical removal of the tumor bearing kidney. Fresh samples originating from normal tissue adjacent to the primary tumors were washed twice in phosphate buffered saline (PBS) and were then placed in 5 ml of 30 mM EDTA. The tissues were minced with a scalpel and filtered through a 54 um nylon mesh [Kunicka et al. 1987]. The cell suspension was centrifuged at 600 g for 5 minutes, the supernatant was discarded, and the pellet was fixed in freshly prepared Carnoy's for 20 minutes at room temperature. Microscope slides were cleaned as described elsewhere [Weier et al. 1991a]. The fixed cells were further washed in two changes of Carnoy's and dropped on the slides. Touching imprints were prepared from frozen tissue samples by pressing the sample against clean glass slides without pretreatment. Cells adhering to the glass were fixed immediately in Carnoy's for 20 minutes.

Pretreatment of fixed kidney cell nuclei was performed with pepsin (100 ug/ml in 0.01N HCl) for 10 minutes at room temperature [Hopman et al. 1989]. The interphase cells were further fixed by a 10 minute immersion in paraformaldehyde [4% (w/v) in PBS]. The slides were then washed in 2×SSC and denatured in 70% formamide, 2×SSC, pH 7.0 for 10 minutes at 72° C. Slides were then dehydrated in a 70%, 80%, and 100% ethanol series, air dried and prewarmed to 37° C. prior to addition of the probe mixture.

f. In Situ Hybridization

Labeled probe DNAs (approximately 20 ng) and selected amounts of unlabeled human genomic DNA or total human alpha satellite DNA were added without purification to 8 ul of the hybridization mixture described by Pinkel et al. 1986. The hybridization protocol was essentially the same as described in Example 1 except that the DNA was denatured after chilling for 5 min. at 74° C. instead of 72° C.; the PI counterstain was used at a concentration of 0.2 ug/ml or 1 ug/ml; and the antifade solution for DAPI was also that of Johnson and de C. Norqueira Arayjo (1981).

Paraffin embedded tissue sections of 4 um thickness were deparaffinized in preparation for in situ hybridization following the protocol of Brigati et al. (1983) that includes the sequential applications of pronase and HCl for tissue processing. The sections were then denatured for 20 min in 70% formamide, 2×SSC at 74° C., dehydrated in a 70%, 80%, 100% ethanol series and hybridized as described above. Post hybridization washes of tissue sections were extended to three times 30 min. in 50% formamide, 2×SSC at 42° C. followed by three washes in PN buffer at 37° C. The tissue sections were then incubated for 20 min. with avidin-FITC as described above, washed in four changes of PN buffer of 15 min. each and mounted in antifade containing 0.5 ug/ml PI.

AAF-labeled probe DNA was detected after incubation with 10 ul of the supernatant from two murine cell lines (MBL4F and MBL6B) that produce monoclonal antibodies against AAF. [Those two cell lines were kindly provided by Dr. R. Baan, TNO, Rijswijk, The Netherlands.] The slides were then washed twice in PN buffer at RT, incubated for 15 min. at RT with a 1:25 dilution of the fluoresceinated goat anti-mouse antibodies in 1xPBS (Mg, Ca free), 2% normal goat serum, 0.05% Tween 20, and washed in two changes of PN buffer at RT.

The detection of digoxigenin-labeled DNA was done with the antibodies against digoxigenin. In these experiments, the digoxigenin-labeled probe was hybridized simultaneously with a biotinylated probe. In some experiments, the uncloned biotinylated chromosome 10 probe was hybridized with a digoxigenin-labeled DNA. The Alu DNA probe was generated from a cloned Alu repeat DNA fragment in a procedure similar to that described herein. The simultaneous hybridization of Alu probes is helpful for chromosome identification due to preferential binding of such probe to specific chromosomal regions in a manner very similar to R-bands [Baldini and Ward 1991]. In other experiments, digoxigenin-labeled probes generated from clonal chromosome 10-specific template DNA were hybridized with the Alu probe labeled with biotin or digoxigenin, respectfully.

Slides were washed in the post-hybridization solutions as described above and blocked by incubation with PNM for 10 minutes at RT. Equal volumes of the fluoresceinated anti-digoxigenin antibody (20 ug/ml in PNM) and avidin-Texas Red (2 ug/ml in PNM) were mixed and applied to the slides. Incubation was performed under a coverslip for 25 minutes at RT in the dark. The slides were then washed in two changes of PN buffer at 37° C. and mounted in DAPI in antifade solution.

Microscopy was performed as indicated in Example 1 wherein the epi-illumination filter was set for FITC allowing the simultaneous observation of PI fluorescence, or a filter was set for simultaneous observation of FITC and TR.

g. PCR Product Cloning

PCR products were amplified for cloning into the Bam HI site of pBS vector (Stratagene, San Diego, Calif.) by resuspending approximately 12,000 flow sorted human chromosomes 10 (1530 per ul) in 400 ul reaction buffer containing primers WA11 and WA12 (shown in Table I) (1.2 uM) in the presence of the four unmodified dNTPs (0.25 mM each) and 8 units of Taq polymerase.

The thermal cycler was programmed to perform an initial 6 cycles with a primer annealing temperature of 40° C., followed by 29 amplification cycles with primer annealing at 50° C. Following DNA amplification, one tenth volume of 5M Na acetate was then added, and the DNA was precipitated in an equal amount of isopropanol, washed with 70% ethanol, air dried and resuspended in 20 ul of 1× Bam HI digestion buffer containing 20 units of Bam H1. The reaction was incubated at 37° C. for 30 min., the DNA was precipitated in 2-propanol and the pellet was washed with 70% ethanol. The PCR products were then resuspended in 100 ul water. Two microliters of the DNA fragments were then resuspended in 30 ul 1× ligase buffer containing 10 units T4 DNA ligase and approximately 1 ug Bam HI-digested pBS DNA. The ligation was done at 15° C. overnight. A 1 ul aliquot of the ligation reaction was diluted 1:5 with 1xTE buffer (10 mM Tris-HCL, 1 mM EDTA, pH 8.0). One microliter of this dilution was used to transform competent DH5 alpha cells according to the supplier's protocol. Bacterial cells were then diluted 1:10 in Luria-Bertani (LB) medium [Maniatis et al. 1986] containing 100 ug/ml ampicillin, and plated on LB agar containing 100 ug/ml ampicillin, 4 ug/ml IPTG and 40 ug/ml X-Gal.

h. Library Screening by PCR

Individual white colonies were picked by using sterile pipette tips and grown in LB broth containing 100 ug/ml ampicillin. A modification of the multiplex PCR protocol [Chamberlain et al. 1888] wherein one pair of primers was used to amplify a number of different DNA sequences was applied. PCR was performed by combining and resuspending four 1 ul aliquots from different overnight cultures in 50 ul amplification buffer containing the primers WBS2 and WBS4, the four unlabeled dNTPs, salts and Taq polymerase as described above for the initial amplification. PCR was performed for 40 cycles with primer annealing at 53° C. Clones that contained PCR products in the desired size range were then individually amplified in 40 cycle PCR reactions by resuspending 1 ul aliquots from the bacterial cultures in 40 ul reaction buffer containing either primer pair WBS2 and WBS4, or WA11 and WA12. Gel electrophoretic analysis of 8 ul aliquots was done in 4% agarose with 200 ng sizemarker DNA ($\phi$X174 RF DNA/Hae III digest) in separate lanes.

i. Generation of Labeled Probes from Bacterial Clones

Amplification products (1 ul) of reactions using cells from representative clones, pBS609-51 and pBS609-52 with the vector-specific primers WBS2 and WBS4 were resuspended in biotinylation buffer containing the insert-specific primers WA11 and WA12. Labeling of the DNA fragments was performed in a 20 cycle PCR as described above. The labeling and simultaneous amplification of PCR products with digoxigenin was performed during 20 cycles similar to the biotinylation reaction, except that the digoxigenin-labeling buffer contained a mixture of digoxigenin-11-dUTP and dTTP (0.16 mM and 0.04 mM, respectively) instead of Biotin-11-dUTP.

In situ hybridization of biotinylated DNA was done as described for the uncloned probe. One microliter of digoxigenin-labeled DNA was mixed with 1 ul of a biotinylated Alu DNA probe, 8 ul MasterMix 2.1 (MasterMix 2.1 is 78.6% formamide, 14.3% dextran sulfate, 2.9×SSC, pH 7.0) and 1 ul herring sperm DNA (10 mg/ml).

j. Probe DNA Sequencing

Plasmid DNA was isolated from 500 ml overnight cultures of bacterial clones in LB-medium using the Maxiprep columns [Qiagen, Studio City, Calif. (USA)] according to the manufacturer's instructions. DNA sequencing was performed by dideoxynucleotide sequencing reactions according to the protocol described by Sanger et al. (1977). Double stranded DNA was sequenced by extension of T3- or T7-primers with dATP, dCTP, dTTP and either dGTP or dITP in the reaction buffer. DNA sequences were read from the original X-ray films. Further processing of the DNA sequences was done using the GeneWorks software obtained from IntelliGenetics, Inc. (Mountain View, Calif.).

Figure 4A:
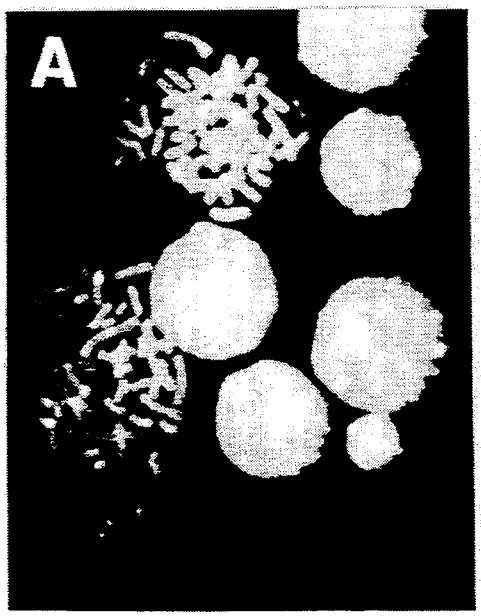
FIG. 4 shows the in situ hybridization of chromosome 10-specific probe DNAs. The biotinylated probe molecules in (A), (C), and (F)-(H) were visualized with avidin-FITC and the AAF-labeled DNA probe shown in (D) and (E) were detected with FITC-conjugated antibodies. DNA was counterstained with propidium iodide. The digoxigenin labeled DNA probes in (B) and (I) were visualized with FITC-conjugated antibodies. The biotinylated probe in (B) was detected using avidin-Texas Red.
Figure 4B:
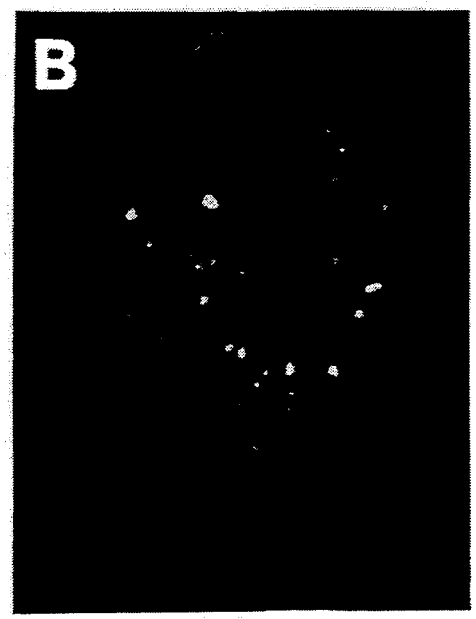

Results k. In Situ Hybridization of Degenerate Probe DNA in the Presence of Blocking DNA Hybridization of a biotinylated chromosome 10-specific probe to normal metaphase spreads in the absence of blocking DNA showed labeling of the centromeric regions on numerous chromosomes (FIG. 4A). Interphase cell nuclei typically showed several fluorescent domains (FIG. 4B).

Figure 4C:
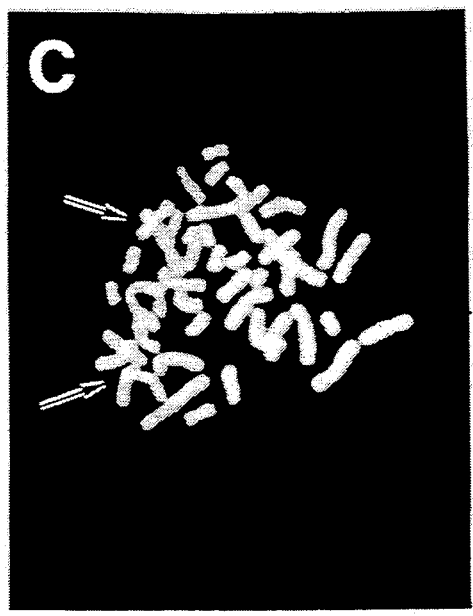
Figure 4D:

The addition of 100 ng of total human alphoid blocking DNA to the hybridization mixture containing approximately 20 ng of biotinylated probe DNA reduced the crosshybridization so that the target chromosomes 10 could easily be identified by their brightly labeled centromeric region (FIG. 4C). Under these conditions, domains containing chromosome 10-specific centromeric DNA could easily be observed and counted in interphase cell nuclei (FIG. 4D). The effect was very similar when 500 ng of human genomic DNA were added to the hybridization cocktail.

Figure 4E:
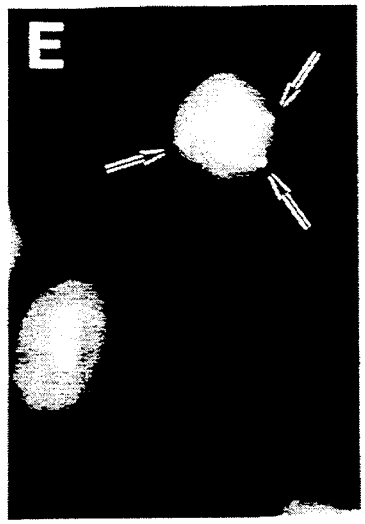

The competitive hybridization regimen using human genomic DNA was used for determining the number of chromosomes 10 in single cell suspensions of kidney tissue adjacent to a surgically removed tumor. The hybridization mixtures typically contained 20 ng of AAF-labeled probe DNA and 500 ng of unlabeled human genomic DNA. Results of the hybridization of the AAF-labeled probe to cell samples from a renal cell carcinoma patient with a tumor karyotype of 47, XY, +10 are depicted in FIGS. 4D and 4E. Cells shown in FIG. 4D showed two bright domains representing chromosome 10-specific alphoid DNA. The interphase cell in FIG. 4E, however, showed three yellow fluorescent domains indicating the presence of an extra copy of chromosome 10 (arrows). Thus, in this particular preparation of single cells, the relative fraction of karyotypically abnormal cells could rapidly be assessed with an approximate error margin of a few percent by counting cells with three domains.

Figure 4F:
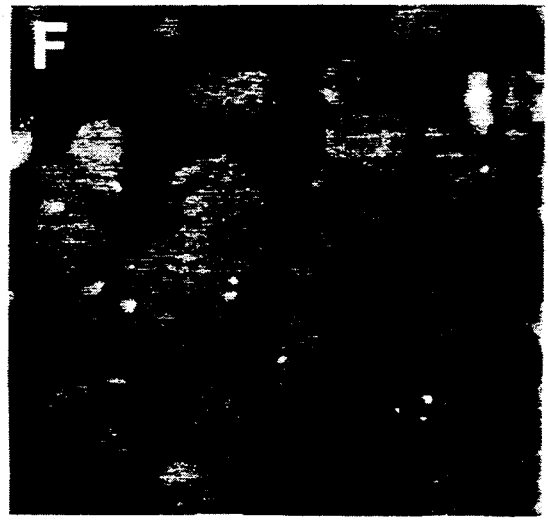

The degenerate probe DNA of this example was applied in a hybridization to deparaffinized tissue sections. The overnight incubation with biotinylated probe was done in the presence of unlabeled human genomic DNA to block cross-hybridization. However, only low levels of cross-hybridization was observed when the blocking DNA was omitted. As shown in FIG. 4F, domains of bound probe DNA could be observed and counted after application of avidin-FITC.

1. Molecular Cloning of the PCR Products and Sequence Analysis.

Recombinant clones were identified as white colonies on ampicillin plates, picked and grown overnight in LB medium containing ampicillin. 64 colonies were selected for further analysis. Bacterial clones were analyzed by multiplex PCR using the vector-specific oligonucleotides WBS2 and WBS4. Gel electrophoresis showed different sized amplification products for several samples. The size of the insert can be derived from the product size by substracting 114 bp, i.e., the distance of the 5'-ends of the primers when annealed to pBS DNA.

Figure 4G:
Figure 4H:
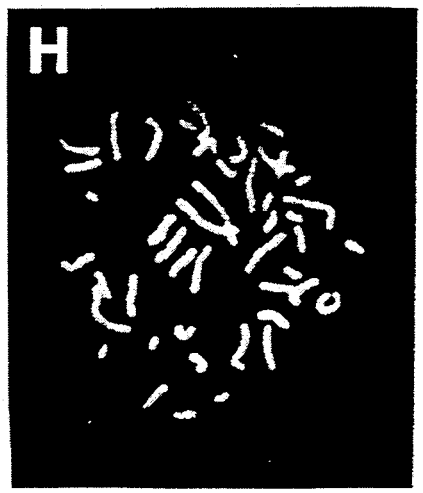
Figure 4I:
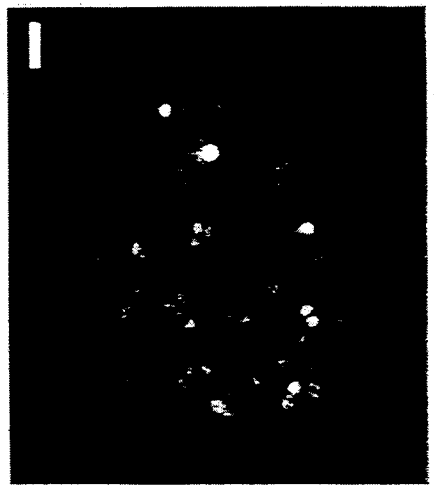

In situ hybridization was performed with probes that were generated by PCR amplification and labeling using the bacterial clones as DNA templates. The biotinylated probes (FIG. 4G and H) as well as the digoxigenin labeled DNA probe (FIG. 4I) showed high signal intensities and specificity with interphase cell and metaphase chromosomes. The intensity on the target chromosomes 10 was at least as high as observed using the degenerate probe; there was, however, no sign of cross-hybridizaton with other chromosomes.

DNA sequencing was performed on DNA isolated from clones pBS609-51 and pBS609-52. The results of DNA sequence analysis are shown in Table II. The sequencing reactions revealed inserts of 191 bp in the Bam H1 sites of pBS609-51 and pBS609-52, respectively. Both inserts are alpha satellite DNA repeat monomers flanked by the PCR primer sequences, and have 87% (pBS609-51) and 88.3% (pBS609-52) homology with the alphoid consensus monomer (Willard and Waye 1987). When 162 bp excluding the 5'-polylinkers were compared with a tetrameric alphoid DNA fragment reported to be chromosomes 12-specific (pBR12; Baldini et al. 1990; EMBL/GenBank accession number M28221), the clones pBS609-51 and pBS609-52 showed high homology with individual monomers. As much as 83.3% (pBS609-51) and 84.6% (pBS609-52) sequence homology was found with the second monomer of pB12 (Table II). The GenBank/EMBO accession numbers for those sequences are X67271 (pBS609-51) and X67272 (pBS609-52).

The results of cloning experiments of chromosome 10-derived alphoid DNA presented in this example suggest the presence of one or several specific monomer sequences. The simple cloning strategy employed for isolation of chromosome 10-specific DNA produced a number of recombinants containing alpha satellite DNA inserts. However, analyses of 64 randomly selected recombinants indicated that there were many small inserts that provide primer annealing sites and possibly represent the small fragments amplified with primers WA11 and WA12 (FIG. 5, lane 3). Further analysis of the DNA inserts is needed to reveal the character and causes of the undesired clones. Among the 64 clones, four clones were found that contained alphoid monomers and hybridize relatively specifically with human chromosome 10.

The library screening procedure using PCR and bacterial cells (Weier and Rosette (1990) is very rapid and efficient. The high sensitivity of PCR allows the pooling and amplification of DNA from more than 4 clones in one reaction (Green and Olsen 1990; Weier et al. 1991c). For rapid screening of colonies, an accelerated protocol similar to the procedure described by Gussow and Clackson (1989) can be used. This scheme allows generation of novel hybridization probes in less than two weeks starting with appropriate oligonucleotides and amplification templates.

TABLE II

DNA sequences of the alphoid consensus monomer[1], the two PCR-isolated chromosome 10-specific alpha satellite DNA clones and four alpha satellite monomers specific for the human chromosome 12[2].

| | | | | | |
|---|---|---|---|---|---|
| Primer WA1 | | GAAGCTTA$^A_T$ | $^G_C$T$^A_C$ACAGAGT | T$^G_T$AA | |
| CONSENSUS [SEQ ID NO: 16] | | AA | CTCACAGAGT | TGAAC$^A_C$TT$^T_C$C | TTTT$^G_C$ATAGA |
| pBS609-51[3] [SEQ ID NO: 17] | GGATCCCTGC | AGAAGCTTAA | GTCACAGAGT | TGAACCTTCC | TTTAGACAGA |
| pBS609-52[3] [SEQ ID NO: 18] | GGATCCCTGC | AGAAGCTTAT | GTAACAGAGT | TGAACCTTCC | TTTAGACAGA |
| I [SEQ ID NO: 19] | | CAA | CTCAAGGTGT | TTAAGCTTTC | TTTTCATAGA |
| II [SEQ ID NO: 20] | | CAA | CTCACAGAGG | TGAACTGTCC | TTTAGACAGA |
| III [SEQ ID NO: 21] | | CAA | TTCACAGAGA | TAACCTTTCT | TTT-GATGAA |
| IV [SEQ ID NO: 22] | | CAA | CTCACAGAGT | TGAACCTTCC | TTTAGACAGA |
| CONSENSUS | GCAGTTT$^G_T$GA | AACACTCTTT | TTGTAGAATC | TGCAAGTGGA | $^T_C$ATTTGGA$^G_C$C |
| pBS609-51 | GCAGTTTTGA | AAAATTCTTT | CTGTGGAATC | TGCAAGTGGA | GATTTCAAGC |
| pBS609-52 | GCAGTTTTGA | AAAACTCTTT | CTGTGGAATT | TGCAAGTGGA | GATTTCAAGC |
| I | GTAGTTTGGA | AACACTCTGT | CTGTAAAGTC | TGCAAGCAGA | TATTTGGACC |
| II | GCAGATGTGA | AACCCTCTTT | TTGTGATATT | TGCAGGTGGA | GATTTCAAGC |
| III | GGAGTTTGGA | GACACTGTGT | TTGTAAAGTC | TGCAAGTGGA | TATTTGGACC |
| IV | GCAGATTTGA | AACACCCTAT | TTGTGCAGTT | TCCAGTTGGA | GATTTCAATC |
| CONSENSUS | $^G_T$CTTTGAGG$^A_C$C | $^T_C$T$^A_T$$^T_C$G$^G_T$TGGA | AA$^A_C$GG$^G_A$AATA | TCTTCA$^T_C$ATA | AAA$^A$_CTA$^G_A$AC |
| pBS609-51 | GATTTGAGGC | TAATCTTTGA | AATGGAAATA | TCCTCGTGTA | AAAACTACAC |
| pBS609-52 | GATTTGAGGC | TAATCTTTGA | AATGGAAATA | TCTTCGTGTA | AAAACTACAC |
| I | TCTTTGGGGC | CTTCGTTGGA | AACGGG-ATT | TCTTCATAGA | A-CGCTAGAA |

TABLE II-continued

DNA sequences of the alphoid consensus monomer[1], the two
PCR-isolated chromosome 10-specific alpha satellite DNA clones and four
alpha satellite monomers specific for the human chromosome 12[2].

| | | | | | |
|---|---|---|---|---|---|
| II | GCTTTTAGGC | CAAATGTAGA | AAAGGAAATA | TCTTCGTATA | AAAACTAGAC |
| III | TCTTTGAGGC | CTTCGTTGGAAGGAAACGGGATT | | TCTTCCTGTA | A-TGTTCGAC |
| IV | ACTTTGAGAC | CAAATGTACA | AAAGGAAACA | TCTTCGTATA | AAAACTAGAC |
| Primer WA2 | | GAAACT$^T$A$_G$ | CTT$^G{}_T$G$^G{}_T$GATC | TGCAGC | |
| CONSENSUS | AGAAGCATTC | TCAGAAACTT | CTTTGTGAT | | |
| pBS609-51 | AGAATCATTC | TCAGAAACTA | CTTGGGGAT<u>C</u> | TGCAGAAGCT | TGGATCC |
| pBS609-52 | AGAATCATTC | TCAGAAACTT | CTTGGTGAT<u>C</u> | TGCAGAAGCT | TGGATCC |
| I | AGAAGAATAC | TGAGTAAGTT | CTTTGTGTTGCCTCTATT | | |
| II | AGAATCATTC | TCAGAAACTA | CTTTGTGATGTGTGCGTT | | |
| III | AGAAGAATTC | TCAGTAACTT | ATTTGTGGTGTGTGTATT | | |
| IV | AGAATCATTC | TCAGAAACTA | CTTTGTGATGTGTGCGTT | | |

[1] The human alpha satellite monomer consensus sequence as defined by Willard and Waye (1987).
[2] I-IV: The chromosome 12-specific alphoid monomer sequences published by Baldini et al. (1990).
[3] The underlined bases represent nonhomologous 5'-polylinker regions of WA11 and WA12, resp.

Example 3

Chromosome-specific Centromeric Probes for Chromosome 17 and Chromosome 3

Two centromere-specific alpha satellite probes were prepared; one specific for the centromeres of chromosome 17 and the other specific for the centromeres of chromosomes 3. The method employed was essentially as described in Examples 1 and 2. The WA1 and WA2 primers were used, and approximately 50 ng of DNA from chromosome 17 was used as the DNA template. The DNA template was isolated from the Bluescribe plasmid library for chromosome 17 (pBS17), which in turn had been prepared by subcloning an entire chromosome 17 library that is publicly available as deposit libraries LL17NS01 or LA17NS03 [Van Dilla et al. 1986].

The DNA amplification and simultaneous biotinylation was performed during 45 cycles using an automated thermal cycling system [Weier and Gray 1988] with a thermal denaturation step of 90 seconds at 94° C. (120 seconds for the initial denaturation). Primer annealing during the second step of each cycle was performed at 53° C. for 90 seconds. The temperature was then increased slowly (7° C./minute) to 72° C. The cycle was completed by holding that temperature for 120 seconds for primer extension.

A probe specific for alpha satellite centromeric repeats on human chromosome 3 was similarly prepared by in vitro DNA amplification using WA1 and WA2 primers and approximately 80 ng of CsCl gradient isolated DNA from the Bluescribe plasmid library for chromosome 3 (pBS3) (400 ng/ml) as amplification DNA template. PCR was performed for 30 cycles using an automated thermal cycler [Perkin-Elmer/Cetus, Norwalk, Conn. (USA)]. The DNA template was denatured at 94° C. for 1 minute. Primer annealing and extension were performed at 53° C. and 72° C. respectively. Probe biotinylation occurred in the presence of Biotin-11-dUTP and further amplification was accomplished during an additional 20 PCR cycles.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

All references herein cited are hereby incorporated by reference.

---

We claim:

1. A method of preparing chromosome-specific repeat sequence nucleic acid probes comprising:
hybridizing a first set of degenerate oligonucleotide primers to DNA strands of repeat sequence units in a template DNA that is chromosome-specific;
hybridizing a second set of degenerate oligonucleotide primers to the DNA strands of said repeat sequence units that are complementary to the DNA strands to which the first set of primers hybridize, such that, if said complementary strands of said repeat sequence units were aligned, and if a primer from both the first and second sets hybridizes within a repeat sequence unit, the 5' end of the primer from the first set faces on the complementary strand the 5' end of the primer from the second set; and such that, if said complementary strands were aligned, the hybridization sites of primers from said first and second sets on their respective complementary strands are within a distance of between about 20 base pairs (bp) to about 5 kilobases (kb);
amplifying the template DNA by a polymerase chain reaction (PCR) method; and
producing chromosome-specific repeat sequence nucleic acid probes by performing one or more of the following steps as necessary: (a) selecting from the PCR products dimers or higher order repeats; (b) adding to said PCR products unlabeled blocking DNA, wherein said blocking DNA is human genomic DNA, Cot 1 DNA and/or human alphoid DNA; and (c) cloning said PCR products and screening the clones for chromosome-specificity, repeat content and/or size;
wherein said first and second primer sets are selected from the group consisting of: Jun1 (SEQ ID NO: 15), WA1 (SEQ ID NO: 1), WA2 (SEQ ID NO: 2), WA11 (SEQ ID NO: 3), and WA12 (SEQ ID NO: 4).

2. A method according to claim 1 wherein said first and second primer sets are selected from the group consisting of WA1 (SEQ ID NO: 1), WA2 (SEQ ID NO: 2), WA11 (SEQ ID NO: 3) and WA12 (SEQ ID NO: 4).

3. A method according to claim 1 wherein said first set of degenerate oligonucleotide primers is the same as said second set of oligonucleotide primers.

4. A method according to claim 3 wherein said first and second primer sets are Jun1 (SEQ ID NO: 15).

5. A chromosome-specific repeat sequence probe prepared by the method of claim 1 and labeled during the amplifying step or thereafter.

6. A method of preparing and amplifying chromosome-specific repeat sequence nucleic acid probes comprising:
hybridizing a first set of degenerate oligonucleotide primers to DNA strands of repeat sequence units in a template DNA that is chromosome-specific;
hybridizing a second set of degenerate oligonucleotide primers to the DNA strands of said repeat sequence units that are complementary to the DNA strands to which the first set of primers hybridize, such that, if said complementary strands of said repeat sequence units were aligned, and if a primer from both the first and second sets hybridizes within a repeat sequence unit, the 5' end of the primer from the first set faces on the complementary strand the 5' end of the primer from the second set; and such that, if said complementary strands were aligned, the hybridization sites of primers from said first and second sets on their respective complementary strands are within a distance of between about 20 base pairs (bp) to about 5 kilobases (kb);
amplifying the template DNA by a polymerase chain reaction (PCR) method;
inserting the products of said PCR amplification into cloning vectors; cloning said PCR products; and screening the clones for chromosome-specificity, repeat content and/or size to select chromosome-specific repeat sequence probes; selecting clones from the group consisting of pBS609-51 which contains SEQ ID NO: 17 as an insert, and pBS609-52 which contains SEQ ID NO: 18 as an insert; and amplifying the selected clones using PCR.

7. A method according to claim 6 wherein the primers used to amplify said selected clones are nondegenerate.

8. A chromosome-specific repeat sequence probe prepared by the method of claim 6 and labeled during the step of amplifying the selected clones or thereafter.

9. A method of preparing chromosome-specific repeat sequence DNA probes by arbitrary selection of repeat DNA sequences from human genomic DNA comprising the steps of:
annealing to human genomic template DNA containing CAGG repeat sequences the degenerate primer Jun1 (SEQ ID NO: 15);
amplifying said template DNA by a polymerase chain reaction (PCR); and
producing chromosome-specific repeat sequence nucleic acid probes by performing one or more of the following steps: (a) selecting from the PCR products dimers or higher order repeats; (b) adding to said PCR products unlabeled blocking DNA, wherein said blocking DNA is human genomic DNA, Cot 1 DNA and/or human alphoid DNA; and (c) cloning said PCR products and screening the clones for chromosome-specificity, repeat content and/or size.

10. A method according to claim 9 wherein said template DNA is chromosome-specific.

11. A chromosome-specific probe prepared by the method of claim 9 and labeled during the amplifying step or thereafter.

12. A composition of matter consisting of an alpha repeat sequence probe specific for chromosome-10 centromeres having the nucleotide sequence for the insert of pBS609-51 (SEQ ID NO: 17) or pBS609-52 (SEQ ID NO: 18) as shown in Table II.

13. A composition of matter comprising a degenerate oligonucleotide set of primers selected from the group consisting of: WA1 (SEQ ID NO: 1), WA2 (SEQ ID NO: 2), WA11 (SEQ ID NO: 3), WA12 (SEQ ID NO: 4), and Jun1 (SEQ ID NO: 15).

* * * * *